United States Patent
DeHarde et al.

(10) Patent No.: US 8,123,709 B2
(45) Date of Patent: *Feb. 28, 2012

(54) AMBULATING KNEE JOINT

(75) Inventors: Mark DeHarde, Pottstown, PA (US); Kenneth A. Patchel, Chadds Ford, PA (US); Thomas Watters, Malvern, PA (US)

(73) Assignee: Ultraflex Systems, Inc., Pottstown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/422,669

(22) Filed: Apr. 13, 2009

(65) Prior Publication Data

US 2009/0198162 A1 Aug. 6, 2009

Related U.S. Application Data

(63) Continuation of application No. 10/423,435, filed on Apr. 25, 2003, now Pat. No. 7,517,330.

(60) Provisional application No. 60/377,119, filed on Apr. 25, 2002, provisional application No. 60/417,268, filed on Oct. 9, 2002, provisional application No. 60/427,777, filed on Nov. 20, 2002, provisional application No. 60/455,809, filed on Mar. 19, 2003.

(51) Int. Cl.
*A61F 5/00* (2006.01)

(52) U.S. Cl. ................ 602/16; 602/20; 602/23

(58) Field of Classification Search ............... 602/5, 16, 602/20–30; 128/882

See application file for complete search history.

(56) References Cited

U.S. PATENT DOCUMENTS

| | | | |
|---|---|---|---|
| 1,847,823 A | 3/1932 | Dresser |
| 2,067,567 A | 1/1937 | Gruca |
| 2,832,334 A | 4/1958 | Whitelaw |
| 2,943,622 A | 7/1960 | Nelson |
| 3,707,963 A | 1/1973 | Keropian |

(Continued)

FOREIGN PATENT DOCUMENTS

EP 0522484 A1 1/1993

(Continued)

OTHER PUBLICATIONS

International Preliminary Examination Report; International Application No. PCT/US03/12887; International Filing Date Apr. 25, 2003; 3 pages.

(Continued)

*Primary Examiner* — Michael A. Brown
(74) *Attorney, Agent, or Firm* — Blank Rome LLP

(57) ABSTRACT

A hinge or joint assembly is provided that includes first and second members, a pivot rotatably connecting the first and second members and allowing movement between extension and flexion positions, and at least one elastomeric spring communicating with the first and second members to restrain pivotal movement of the members toward flexion, through compression of the elastomeric spring, and to assist pivotal movement toward extension through decompression of the elastomeric spring. The assembly can further include a disk and lock slide, the disk and lock slide each having complementary teeth providing, when engaged, an arrest of pivotal movement in a direction of flexion and one-way, ratcheting, step-advance pivotal movement in a direction toward extension. The elastomeric spring can be urethane, and can be adapted to mimic any bodily muscle. An embodiment employing a torsional spring is also provided, as is a cable release mechanism providing one-dimensional cable movement.

12 Claims, 18 Drawing Sheets

U.S. PATENT DOCUMENTS

| | | |
|---|---|---|
| 3,814,419 A | 6/1974 | Bjorklund et al. |
| 3,826,251 A | 7/1974 | Ross |
| 4,252,111 A | 2/1981 | Chao et al. |
| 4,310,154 A | 1/1982 | Kauffman |
| 4,340,041 A | 7/1982 | Frank |
| 4,397,308 A | 8/1983 | Hepburn |
| 4,485,808 A | 12/1984 | Hepburn |
| 4,489,718 A | 12/1984 | Martin |
| 4,493,316 A | 1/1985 | Reed et al. |
| 4,502,472 A | 3/1985 | Pansiera |
| 4,508,111 A | 4/1985 | Hepburn |
| 4,538,600 A | 9/1985 | Hepburn |
| 4,614,181 A | 9/1986 | Karlsson |
| 4,633,867 A | 1/1987 | Kausek et al. |
| 4,657,000 A | 4/1987 | Hepburn |
| 4,681,097 A | 7/1987 | Pansiera |
| 4,697,583 A | 10/1987 | Mason et al. |
| 4,726,361 A | 2/1988 | Farley |
| 4,738,252 A | 4/1988 | Friddle et al. |
| 4,771,768 A | 9/1988 | Crispin |
| 4,802,467 A | 2/1989 | Pansiera |
| 4,817,588 A | 4/1989 | Bledsoe |
| 4,844,057 A | 7/1989 | Hoy |
| 4,846,842 A | 7/1989 | Connolly et al. |
| 4,865,024 A | 9/1989 | Hensley et al. |
| 4,928,676 A | 5/1990 | Pansiera |
| 4,938,206 A | 7/1990 | Harris et al. |
| 4,958,643 A | 9/1990 | Pansiera |
| 4,961,416 A | 10/1990 | Moore et al. |
| 4,982,732 A | 1/1991 | Morris |
| 5,000,169 A | 3/1991 | Swicegood et al. |
| 5,002,044 A | 3/1991 | Carter |
| 5,013,037 A | 5/1991 | Stermer |
| 5,025,801 A | 6/1991 | Callaway |
| 5,031,606 A | 7/1991 | Ring, Sr. |
| 5,036,837 A | 8/1991 | Mitchell et al. |
| 5,092,321 A | 3/1992 | Spademan |
| 5,103,807 A | 4/1992 | Makaran |
| 5,117,814 A | 6/1992 | Luttrell et al. |
| 5,121,747 A * | 6/1992 | Andrews ............................. 607/2 |
| 5,144,943 A | 9/1992 | Luttrell et al. |
| 5,188,584 A | 2/1993 | Petrofsky et al. |
| 5,209,716 A | 5/1993 | Frydman et al. |
| 5,313,942 A | 5/1994 | Platzker |
| 5,358,469 A | 10/1994 | Patchel et al. |
| 5,364,323 A | 11/1994 | Liu |
| 5,382,224 A | 1/1995 | Spangler |
| 5,399,154 A | 3/1995 | Kipnis et al. |
| 5,401,235 A | 3/1995 | Devens |
| 5,409,449 A | 4/1995 | Nebolon |
| 5,421,810 A | 6/1995 | Davis et al. |
| 5,454,769 A | 10/1995 | Chen |
| 5,460,599 A | 10/1995 | Davis et al. |
| 5,476,435 A | 12/1995 | Nimmo |
| 5,538,499 A | 7/1996 | Schwenn et al. |
| 5,658,241 A * | 8/1997 | Deharde et al. ................... 602/5 |
| 5,662,595 A | 9/1997 | Chesher et al. |
| 5,681,267 A | 10/1997 | Molino et al. |
| 5,683,353 A * | 11/1997 | Hamersly ....................... 602/16 |
| 5,749,840 A | 5/1998 | Mitchell et al. |
| 5,776,086 A | 7/1998 | Pansiera |
| 5,830,166 A | 11/1998 | Klopf |
| 5,891,061 A | 4/1999 | Kaiser |
| 5,899,869 A | 5/1999 | Barrack, Jr. et al. |
| 6,010,474 A | 1/2000 | Wycoki |
| 6,080,123 A | 6/2000 | Pansiera |
| 6,471,664 B1 | 10/2002 | Campbell et al. |
| 6,517,503 B1 | 2/2003 | Naft et al. |
| 6,764,244 B2 | 7/2004 | Pansiera |
| 6,827,343 B2 | 12/2004 | Skiera |
| 7,517,330 B2 | 4/2009 | DeHarde et al. |
| 2002/0026136 A1 | 2/2002 | Weihermuller |
| 2007/0270976 A1 | 11/2007 | DeHarde |

FOREIGN PATENT DOCUMENTS

| | | |
|---|---|---|
| JP | H06003309 | 1/1994 |
| JP | H08511975 | 12/1996 |
| JP | H9502366 | 3/1997 |
| JP | H10500602 | 1/1998 |
| JP | 10138366 | 5/1998 |
| JP | 11508167 | 7/1999 |
| JP | 200333377 | 2/2003 |
| WO | 9501141 | 1/1995 |
| WO | 9501769 | 1/1995 |
| WO | 9700661 | 1/1997 |
| WO | 0112110 A1 | 2/2001 |

OTHER PUBLICATIONS

List of References Cited; Japanese Patent Office; Dec. 11, 2007.

* cited by examiner

AMBULATING KNEE JOINT

RELATED APPLICATIONS

This application is a continuation of U.S. patent application Ser. No. 10/423,435 (now U.S. Pat. No. 7,517,330), filed Apr. 25, 2003, entitled "AMBULATING KNEE JOINT," which claims benefit of the following U.S. Provisional Applications: Application Ser. No. 60/377,119, filed Apr. 25, 2002, entitled "AMBULATING KNEE JOINT WITH RANGE OF MOTION (ROM) DISC AND OVERRIDE FEATURE;" Application Ser. No. 60/417,268, filed Oct. 9, 2002, entitled "AMBULATING KNEE JOINT;" Application Ser. No. 60/427,777, filed Nov. 20, 2002, entitled "AMBULATING KNEE JOINT;" and Application Ser. No. 60/455,809, filed Mar. 19, 2003, entitled "AMBULATING KNEE JOINT." The above-noted related applications are each incorporated herein, in their entirety, by reference.

FIELD OF THE INVENTION

The present invention relates generally to hinge or joint devices, and more particularly to a hinge or joint assembly for an orthotic, prosthetic, or rehabilitative device capable of supporting the human frame with dynamic shock absorption when walking, while enabling normal, or close to normal, ambulatory motions.

BACKGROUND OF THE INVENTION

A description of a typical human walking cycle (i.e., gait) begins with a heel strike to the ground, followed by a mid-stance phase in which the front of the foot lowers to the ground, pivoting about the grounded heel. The gait then transitions to a toe-off phase, in which the heel is lifted with an associated forward motion of the leg and body on the ball and toes of the foot. Ultimately, the foot is completely lifted from the ground and swung forward in a swing-through phase to the next heel strike. The other foot undertakes the same cycle of motion in a generally coordinated manner to provide forward locomotion.

During this complex motion, each knee transitions from a relatively straight extension at heel strike to a rearward bend, or flexion, through the toe-off phase, and returns to extension during the final swing-through phase. During the cycle, the weight of the patient is borne through the knee to varying degrees.

The human knee system can suffer a number of pathologies that affect the patient's ability to bear this weight and walk (with or without pain). Orthotic knee devices are primarily directed to supporting and stabilizing the knee in response to muscle weakness and/or joint instability. The devices support, guide, and limit the range of motion of the knee joint during the gait cycle. However, traditional orthotic devices are prone to rigidity in movement, and do not provide flexion and extension capabilities approximating that of a healthy, normal knee. For instance, during a normal walking motion, there exists a certain degree of muscle resistance during knee flexion, and a certain degree of shock absorption by the quadriceps, upon heel strike, thereby causing knee flexion and preventing the impact from permeating up the leg to the hips and back, as can occur with a stiff-legged, strutting gait.

For the foregoing reasons, it is an objective of orthotic devices to provide fundamental support, while additionally providing versatility of motion that, to the greatest extent possible, resembles normal joint and muscle function to absorb ground reaction forces and redirect them toward forward progression. Further, au orthotic device closely approximating normal joint and muscle motion can help prevent a learned disuse of certain muscles and movements during a period of prolonged immobility and/or rehabilitation, whereby the brain settles on compensatory muscle use and movements that greatly inhibit mobility, eventually requiring heavier and more restrictive devices resulting in more noticeable limp and an inefficient gait.

SUMMARY OF THE INVENTION

The present invention provides an orthotic, prosthetic, or rehabilitative device that assists, or takes the place of, muscles that are weak or absent, and that normally control and prevent the knee from lagging during swing-through extension, from buckling at heel strike through terminal stance on the balls and toes of the foot, and from buckling during sit-to-stand from a chair. The device of the present invention provides controlled, multi-position rotational motion in the extension direction to prevent knee buckling from sit-to-stand through a ratcheting, step-advance feature. Further, resistance to knee flexion is provided through an elastomeric spring, enabling a dampening shock absorption feature, the elastomeric spring also assisting knee movement from a flexed attitude during the swing-phase to a straight leg position (extension) just prior to initial contact with the floor (heel strike). Elastomeric material characteristics further enable relatively high stance control moments to be effectively dampened, while swing return moments and rate of return (or hysteresis) are far less in magnitude and velocity, thereby mimicking normal muscle function.

The present invention provides a weight bearing strut assembly capable of supporting the human frame in the act of walking, while enabling a leg to which it is attached to bend in a normal and natural ambulatory manner. While walking, the present invention provides shock absorption during heel strike and an accelerating or urging capability to a forward moving lower leg during swing from knee flexion to extension in preparation for receiving weight upon heel strike. Both the dampening, shock absorption function and the urging capability or force is adjustable, with a degree of force and angle of rotation upon which the force is provided being adaptable to suit individual needs. The present invention incorporates the normal and natural ambulatory motion with the security of a step-advance feature, ensuring support of the knee during weight bearing extension (e.g., rising from a sitting position). The elastomeric spring can be adapted to reproduce the force deflection curve of any bodily muscle, by varying the size, shape, and/or characteristics of the elastomeric spring.

The principles and concepts of the present invention can be used in hinge and joint assemblies generally, can be used in an orthotic and/or rehabilitative embodiment as taught and described herein, or can be used in a prosthetic embodiment as modified by those with skill in the art from an appreciation of the present invention. Further, in addition to use in joint and hinge assemblies generally, the present invention can be specifically directed to devices supporting any flexible ligamentous joint, such as the ankle, elbow, or shoulder, and can be adapted to mimicking, assisting, and/or supporting any muscle or tissue, including providing adjustable corrective or therapeutic force for the reduction of joint and muscle stiffness, contracture, or for management of spasticity.

In one aspect of the present invention, a hinge assembly includes a first member movably connected to a second member to allow angular displacement of the first member relative to the second member between extension and flexion positions, and at least one elastomeric spring communicating with the first and the second members to restrain angular displacement from an extension to a flexion position, or from a flexion to an extension position, through compression of the at least one elastomeric spring, and to assist angular displacement from a flexion to an extension position, or from an extension to a flexion position, through decompression of the at least one elastomeric spring. The elastomeric spring can be adapted to provide a pre-determined force deflection curve in compression and an independent rate of return hysteresis in decompression. The elastomeric spring could be a urethane spring.

In another aspect of the present invention, the hinge assembly includes a first member movably connected to a second member to allow angular displacement of the first member relative to the second member between extension and flexion positions, and at least one spring communicating with the first and the second members to dampen angular displacement from an extension to a flexion position, or from a flexion to an extension position, through compression of the at least one spring, and to urge angular displacement from a flexion to an extension position, or from an extension to flexion position, through decompression of the at least one spring, wherein a time late of compression of the at least one spring in response to a force is faster than a subsequent time rate of decompression of the at least one spring resulting from the force. In this aspect, the at least one spring could be an elastomeric or a torsion spring.

In another aspect of the present invention, the hinge assembly is adapted for an orthotic, prosthetic, or rehabilitative device, and includes a proximal member movably connected to a distal member to allow angular displacement of the proximal member relative to the distal member, a spring housing communicating with the proximal and the distal members, where movement of the spring housing tracks, and is tracked by, movement of one of the proximal or the distal members. In this aspect, the hinge assembly further includes at least one elastomeric spring in bearing engagement with the spring housing, wherein angular displacement of the proximal member relative to the distal member in a first direction compresses the at least one elastomeric spring to dampen the angular displacement in the first direction, where decompression of the at least one elastomeric spring urges angular displacement of the proximal member relative to the distal member in a second direction. The spring housing can include a channel to keep each elastomeric spring, each elastomeric spring then compressing against inner walls of the channel.

In another aspect of the present invention, the hinge assembly is again adapted for an orthotic, prosthetic, or rehabilitative device, and includes a proximal member movably connected to a distal member to allow angular displacement of the proximal member relative to the distal member between extension and flexion positions, and a disk and a lock slide communicating with the proximal and the distal members, the lock slide and the disk adapted for engagement to one another. In this aspect, engagement of the lock slide with the disk over a first pre-determined range arrests angular displacement of the proximal member relative to the distal member in a direction toward flexion, and provides one-way, ratcheting step-advance in a direction toward extension. Further, angularly displacing the disk relative to the proximal and the distal members over a second pre-determined range provides free angular displacement of the proximal member relative to the distal member in a direction toward flexion and toward extension, the free angular displacement occurring over the second pre-determined range even if the lock slide is positioned for engagement of the disk.

In this aspect, the second pre-determined range could be adjustable between approximately 0° to 30° of free angular displacement of the proximal member relative to the distal member in a direction toward flexion and toward extension. The second pre-determined range could occur when the proximal member is positioned between approximately 150° to 180° relative to the distal member. Further, the first pre-determined range could be adjustable between approximately 90° to 120° of angular displacement of the proximal member relative to the distal member in a direction toward flexion and toward extension. The first pre-determined range could occur when the proximal member is positioned between approximately 60° to 180° relative to the distal member.

In this aspect, the hinge assembly could further include a worm gear, and the disk a plurality of worm teeth, the worm gear and the worm teeth being engagably positioned so that operation of the worm gear engages and turns the worm teeth to angularly displace the disk relative to the proximal and the distal members to set the first and the second pre-determined ranges. The lock slide could further includes one or more slide teeth and the disk a plurality of disk teeth, the lock slide engaging the disk by an interlocking of the slide teeth with the disk teeth, the disk teeth and the worm teeth each lying about a perimeter of the disk in a similar plane.

In another aspect of the present invention, a cable release mechanism is provided for an orthotic, prosthetic, or rehabilitative device, and includes an actuator rotatable about an axis and linearly translatable relative to a bearing surface, the actuator having a projecting cam surface and a first and a second operating surface, the cam surface positioned between the first and the second operating surfaces, the cam surface located a greater distance from the axis than the second operating surface, the second operating surface located a greater distance from the axis than the first operating surface, the actuator communicating with a cable and a desired first engagable, and releasably movable, component of the device, the first engagable component releasably moving to engage a second engagable component of the device.

In this aspect, positioning the first operating surface against the bearing surface positions the cable to allow the first engagable component to engage the second engagable component. Positioning the second operating surface against the bearing surface linearly translates the actuator, relative to the bearing surface, to linearly retract the cable, relative to the second engagable component, a distance adequate to disengage the first engagable component from the second engagable component. Finally, positioning the cam surface against the bearing surface linearly translates the actuator, relative to the bearing surface, to linearly retract the cable, relative to the second engagable component, a distance greater than that necessary for positioning either the first or the second operating surface against the bearing surface, thereby causing a toggle action and snap, under cable tension, when moving through cam surface engagement with the bearing surface to either of the first or the second operating surface engagement with the bearing surface, to provide a user with positive and certain positioning of the cable release mechanism. The cable release mechanism could be adapted for employment with any of the hinge assemblies of the present invention.

In another aspect of the present invention, an orthotic, prosthetic, or rehabilitative device is presented and includes a proximal member rotatably connected to a distal member by a hinge assembly, the hinge assembly allowing angular displacement of the proximal member relative to the distal member to and from extension and flexion positions. In this aspect, the hinge assembly includes a disk, a lock slide adapted for engaging the disk, where engagement of the lock slide with the disk, over a first pre-determined range, arrests angular displacement of the proximal member relative to the distal member in a direction toward flexion, and provides one-way, ratcheting step-advance in a direction toward extension. The hinge assembly of this aspect further includes at least one spring communicating with the proximal and the distal members, over a second pre-determined range, to provide a dampening of angular displacement of the proximal member relative to the distal member in a direction toward flexion, and to provide an urging of angular displacement in a direction toward extension. The at least one spring could be a torsion spring or an elastomeric spring.

In this aspect, the hinge assembly could also include a mechanism having a catch, the mechanism angularly communicating with the disk and the proximal and the distal members, where engagement of the lock slide within the catch facilitates the dampening of angular displacement in a direction toward flexion and the urging of angular displacement in a direction toward extension. The mechanism could be a spring housing, the spring housing having a channel to keep each spring, each spring compressing against walls of the channel to dampen the angular displacement in a direction toward flexion and decompressing from walls of the channel to urge the angular displacement in a direction toward extension. Further, at least one post could be fixedly connected to the disk and could extend perpendicularly from a face thereof, each post extending into a respective channel of the spring housing, where each post forcibly bears against a respective spring to compress the spring against the walls of the channel and against the face of the disk to dampen the angular displacement in a direction toward flexion, the spring decompressing against and forcibly moving each post to urge the angular displacement in a direction toward extension. Angular displacement of the spring housing could track, and be tracked by, angular displacement of one of the proximal or the distal members.

In this aspect, as an alternative to the mechanism having a catch, the hinge assembly could include a rotor having at least one end tooth, the rotor angularly communicating with the disk and the proximal and the distal members, where engagement of the lock slide with the at least one end tooth facilitates the dampening of angular displacement in a direction toward flexion and the urging of angular displacement in a direction toward extension. In this aspect having a rotor, the hinge assembly could further include a spring housing having a channel to keep each spring, each spring compressing against walls of the channel to dampen the angular displacement in a direction toward flexion and decompressing from the walls of the channel to urge the angular displacement in a direction toward extension. In this aspect having a rotor, angular displacement of the rotor could cause the rotor to bear against each spring to forcibly compress each spring against the walls of the channel.

In another aspect of the present invention, angular displacement of the proximal member relative to the distal member occurs by rotation about a single pivot point. In this aspect, the disk could be rotatable about the single pivot point to set the first and the second pre-determined ranges. In this aspect, the first pre-determined range could be approximately 90° to 120° about the pivot point, and could occur when the proximal member lies about the pivot point between approximately 60° to 180° relative to the distal member. Further, the second pre-determined range could be approximately 0° to 30° about the pivot point, and could occur when the proximal member lies about the pivot point approximately 150° to 180° relative to the distal member. In this aspect having a single pivot point, the at least one spring could be a torsion spring or an elastomeric spring.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings certain embodiments of the present invention. It should be understood, however, that the invention is not limited to the precise arrangements and instrumentalities shown. In the drawings, the same reference numerals are employed for designating the same elements throughout the several figures. In the drawings:

FIG. 3b illustrates an underside, perspective, exploded view of the hinge assembly of FIG. 3a;

FIG. 4b illustrates a back, or underside, perspective, exploded view of the cable release mechanism of FIG. 4a;

FIG. 5e illustrates a front elevation view of the binge assembly of FIG. 1 in a position of full flexion, with the slide teeth again engaging the spur teeth to provide one-way, step advance ratcheting of rotational movement toward extension, FIG. 5e also illustrating the ROM disk set for a 30° range of motion, with elastomeric springs at rest (no pre-load) due to spring post positioning within the respective channels;

FIG. 7b illustrates an underside, perspective, exploded view of the hinge assembly of FIG. 7a;

FIG. 9b illustrates an overhead, or front-side, perspective, exploded view of the hinge assembly of FIG. 9a.

DETAILED DESCRIPTION OF THE INVENTION

Figure 1:
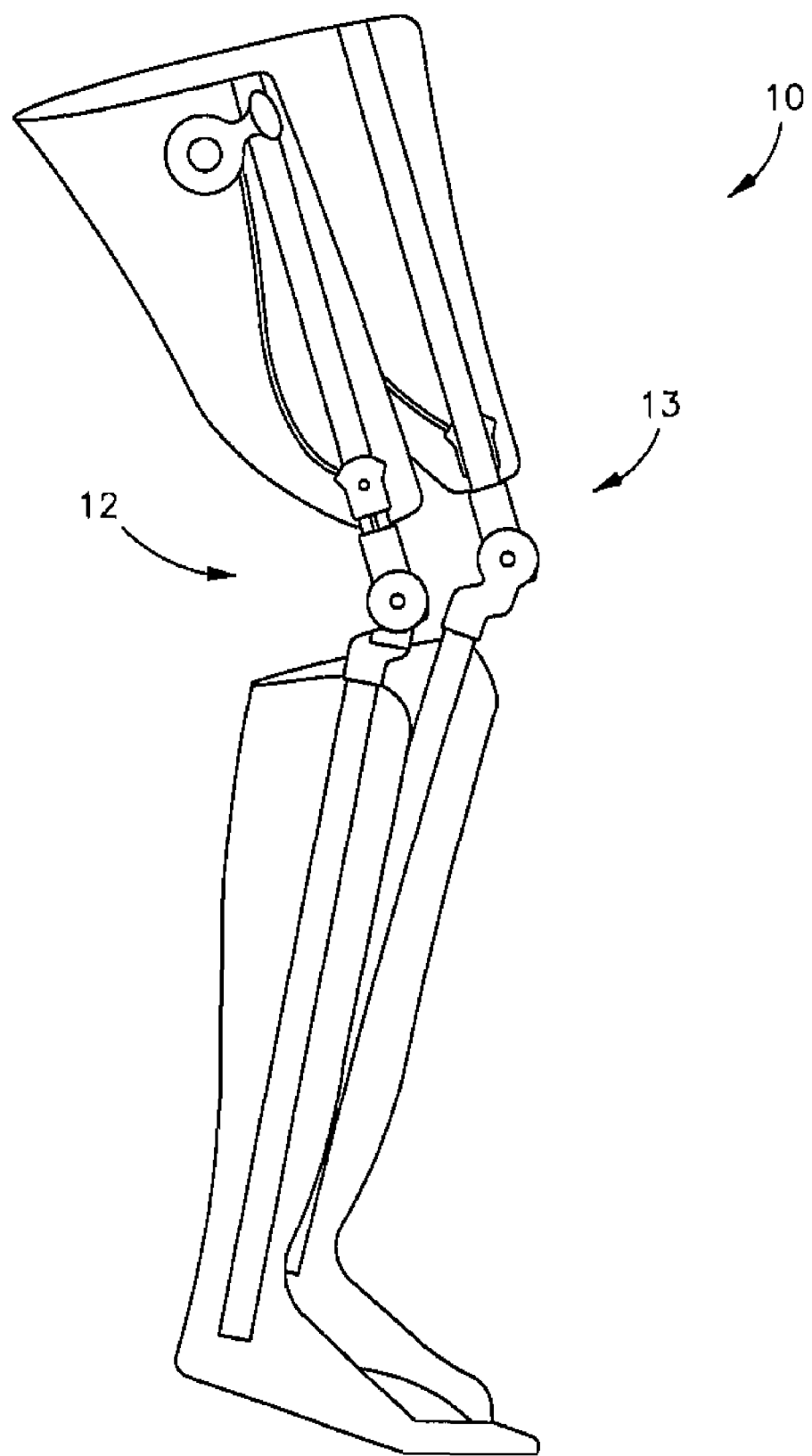
FIG. 1 illustrates an orthotic knee brace for the right leg in accordance with one embodiment of the present invention.

The present invention is a joint or hinge assembly generally, and more particularly an ambulating knee joint having several embodiments, functioning to address various problems while offering advantageous rehabilitative capabilities. Embodiments of the present invention include one or more of the following features:

dynamic shock absorption at initial contact (i.e. heel strike) to dampen ground reaction forces and loading responses, for smoother knee flexion during gait;

swing assist to achieve full terminal swing in the presence of extensor weakness, thereby ensuring that the heel hits the ground first (rather than the mid or forefoot);

sit-to-stand support from a chair, for those having difficulty rising from a sitting position, through a one-way, step-advance ratchet from full flexion (approximately 120° flexion) to full extension, that allows knee extension but prevents knee buckling by locking if the knee begins flexion before reaching a standing position;

an adjustable range of motion, adjustable between typical flexion angles experienced during stance phase of gait (e.g., between 0-30° in current exemplary use), the adjustable range of motion defining an operating range for the variably controlled knee flexion (without knee locking) and extension during walking or standing through use of a range of motion (ROM) disc adjusted by a worm gear, the ROM disc allowing knee flexion, but also arresting flexion if the knee buckles (e.g., due to weak quadriceps) beyond the set point of the range of motion, arresting flexion thereby preventing a fall;

an elastomeric spring providing variable force deflection curves to mimic desirable muscle responses, providing variable restraint of flexion and assisting extension at various angles of flexion and extension; and a lever lock employing a toggle cam to engage and disengage the sit-to-stand, one-way, step-advance ratchet support, the 0-30° controlled knee flexion/extension with elastomeric spring shock absorption and swing assist, and a release enabling free-rotation (a ROM disc override) for sitting, the lever adapted for easy "pushing" by the knuckles or "raking" by the clawed fingers of an impaired hand (e.g., by stroke), the "pushing" and "raking" requiring little finger force, sensation or dexterity as gross elbow movement is employed, the clawed fingers remaining in a natural resting position, the toggle and cam providing visual, sensory and auditory feedback that the lock is properly engaged or disengaged, the lever assembly being low profile for actuation under clothing. The toggle cam also provides fine adjustment to properly tension cable release for engagement and disengagement.

Exemplary Uses of the Present Invention

The present invention can be used in any joint or hinge assembly, particularly those benefiting from a dampening and/or resisting of two members angularly moving closer to one another, and an urging and/or assisting of the two members angularly extending away from one another. Further, the present application has applicability in any muscle adaptation system, such as in robotics, as the elastomeric spring can be adapted to mimic any bodily tissue and/or musculature. Additionally, any flexible ligamentous joint can be supported and assisted (orthotics), rehabilitated, or replaced (prosthetics) with an adaptation of the present invention.

More particularly, in one embodiment the present invention satisfies the rehabilitation needs of a stroke patient. Stroke patients often suffer a partial, temporary, or permanent paralysis to one side of the body. Accordingly, muscle strength, control, and coordination are reduced. During rehabilitation, the patient is encouraged to walk as much as possible to re-train, control and re-strengthen the muscles, and to stimulate the neuro-plasticity of the brain to re-learn to walk. Patients often lack the necessary confidence and strength to walk without falling; such a patient could be fitted with an orthotic knee brace employing an embodiment of the present invention.

In this embodiment, the joint would likely be set, initially, with a 0° range of motion. As such, the knee is locked in full extension, giving the patient stability in stance, and a confidence that they will not fall due to knee buckling. As rehabilitation progresses some range of motion would be allowed, and then would be incrementally increased as the hinge assembly of the present invention can be adjusted to enable between 0-30° of flexion in infinite degree increments. Incrementally increasing the range of motion during rehabilitation enables a re-development of a normal gait, while still offering support if the knee fails to prevent knee bucking.

In another embodiment, and perhaps in the orthotic embodiment above, an extension moment at the knee assists the limb in the swing-phase of gait, thereby helping the knee reach full extension for muscle reeducation, strengthening, and cortical retraining. This embodiment could further include restraint of flexion, providing dynamic shock absorption at initial contact (i.e. heel strike) to dampen ground reaction forces and loading responses for smoother knee flexion during gait, such as in forced limb use programs, stroke rehabilitation, and in any permanent extensor weakness causing knee instability and buckling.

Other potential uses for the brace include any condition (neurological or orthopedic), which weakened the extensor mechanisms, preventing the patient from reaching full extension during walking or causing knee buckling during stance when the limb bears weight.

The joint can be mounted either on a traditional metal and leather KAFO, or a molded plastic or composite brace. Mounts could accommodate ¾×3/16 or ¾×¼ in aluminum or stainless steel uprights, or some other type of connector to be used with composite or molded brace construction.

An Exemplary Embodiment of the Present Invention

One embodiment of the invention incorporates a hinge assembly into an ambulating knee joint having an elastomeric spring dampening system that cushions weight-bearing shock during walking, dampening flexion, and assists leg extension during the swing-phase of gait. The dampening and swing assist moments operate within a range of motion as provided by a range of motion (ROM) disk and determined by an adjustable worm gear mechanism. In this embodiment, the range of motion can be set between 0° and 30°, adjustable therein depending on the strength and needs of the patient (i.e., as the patient becomes stronger, less support is needed, and the range of motion can usually be increased). The dampening and swing assist forces within this range of motion can also be adjusted to individual needs to sufficiently provide a moment at each swing through phase of gait and to provide shock absorption for smoother walking by redirecting forces toward forward progression to reduce an energy cost of walking for the patient.

Please note that although the following exemplary embodiments illustrate angular displacement of a first, or proximal, member relative to a second, or distal, member about a pivot point, and illustrate angular movement capability of other components (e.g., a disk, a spring assembly) about the same pivot point, the present invention is not limited to such structure. The present invention includes, and features of the present invention are applicable to, hinge assembly angular articulation about instance centers, eccentric surfaces, polycentric and multicentric axes, a plurality of camming surfaces, etc.

Further, the exemplary embodiments detailed below illustrate a dampening of angular displacement, or articulation, in a direction of flexion, and an urging of angular displacement in a direction of extension. The present invention is also not limited to such directional requirements, the present invention contemplating dampening and assisting in any direction. Accordingly, the present invention further includes, and features of the present invention are applicable to a dampening, restricting, or restraining of angular displacement from a flexion to an extension position, and/or an assisting, or urging, of angular displacement from an extension to a flexion position.

FIG. 1 illustrates an orthotic knee brace 10 adapted for a right leg ("right hand"), the knee brace 10 incorporating one embodiment of the joint or hinge assembly of the present invention. The knee brace 10 includes right hand lateral joint assembly 12 and a right hand medial joint assembly 13. The joint assemblies function similarly, whether right hand lateral, right hand medial, left hand lateral, or left hand medial, the differences simply being orientation of the respective device relative to its position, particularly effected is the orientation of a distal half joint (described below).

Figure 2:
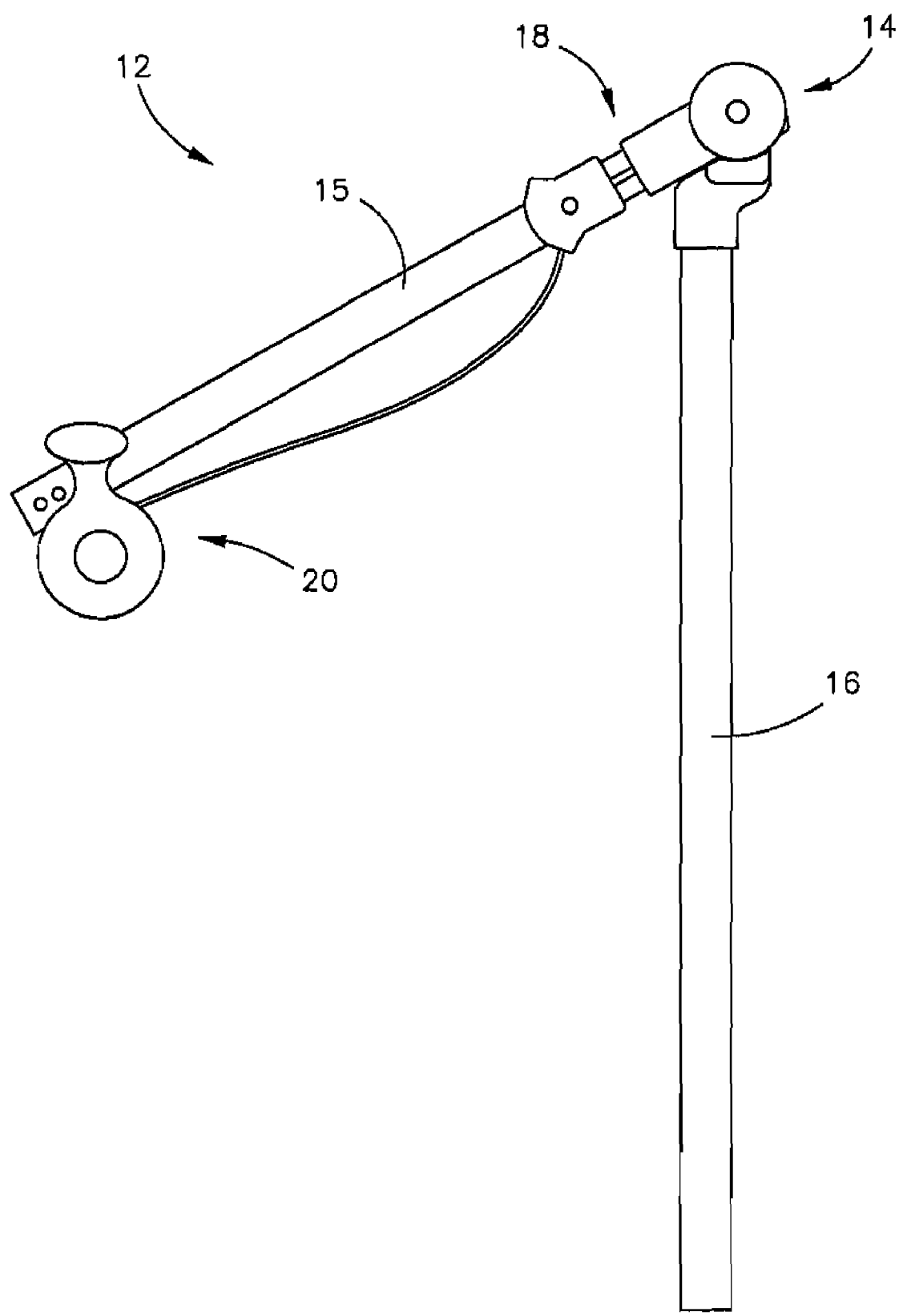
FIG. 2 illustrates a lateral, right-hand hinge assembly with cable release mechanism, and accompanying lateral struts, of the knee brace of FIG. 1.

FIG. 2 illustrates the right hand lateral joint assembly 12 of the orthotic knee brace 10. The joint assembly 12 includes a hinge assembly 14, a proximal strut, or upper member 15, a distal strut, or lower member 16, a lock slide assembly 18 with associated cable release mechanism 20.

Figure 3A:
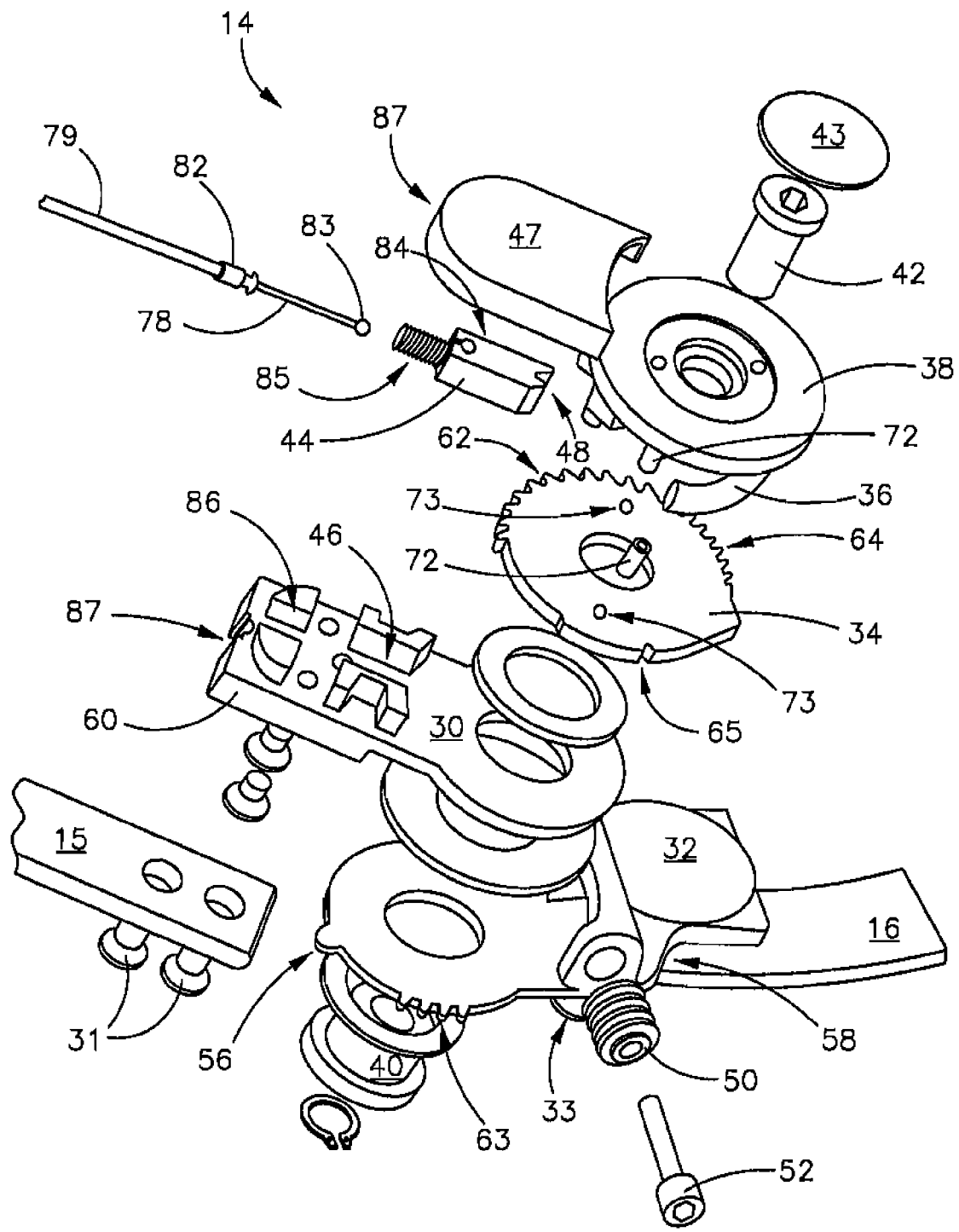
FIG. 3a illustrates an overhead, or front-side, perspective, exploded view of a lateral, left-hand hinge assembly in accordance with one embodiment of the present invention.
Figure 3B:
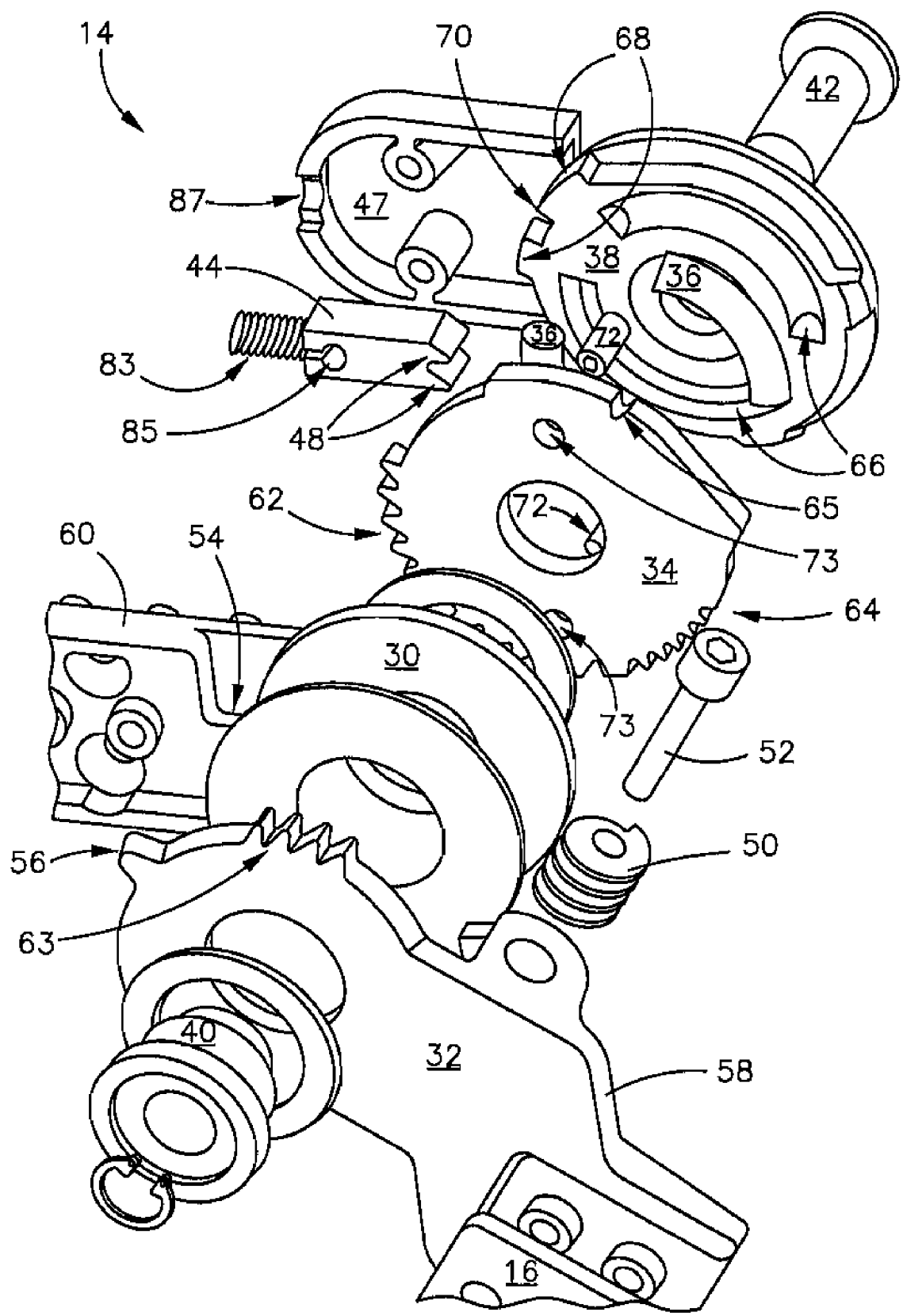

FIGS. 3a and 3b are exploded views of the hinge assembly 14, FIG. 3a being a top, or front side perspective exploded view, FIG. 3b being a bottom, or underside perspective exploded view. Further, the exploded views of FIGS. 3a and 3b actually illustrate a left hand lateral hinge assembly. The hinge assembly 14 includes a proximal half joint 30, fixedly attached to the upper member 15 with screws 31, a distal half joint 32, fixedly attached to the lower member 16 with screws 33, a range of motion (ROM) disk 34, elastomeric springs 36, and a spring housing 38. Certain hinge assembly 14 components are rotatably secured to one another by a pivot post 40 and a break pin 42, with various washers interleaved between the components to facilitate rotational movement, provide wear resistance, remove tolerance build up in thicknesses and length of the pivot post 40 and break pin 42. An aesthetic cover 43 fits within a recess in the spring housing 38 to cover the break pin 42 and recess to hinge disassembly.

The proximal half joint 30 houses components of the lock slide assembly 18, the lock slide assembly 18 enabling a rotational step-advance feature when the hinge assembly 14 pivots from a flexion to an extension position. A lock slide 44 is translatably housed within a rectangular recess 46 in the proximal half joint 30 and secured therein by a lock slide cover 47. The lock slide 44 translates linearly within the rectangular recess 46 through a center-line directed toward and through a pivot point of the hinge assembly 14, the pivot point defined by the pivot post 40 and generally by a center of circular portions of the hinge assembly 14 components. The lock slide 44 includes, at its distal ends one or more slide teeth 48.

The distal half joint 32 houses a worm gear 50, rotatably attached to the distal half joint 32 by a worm gear screw 52. The worm gear 50 interlocks with the worm gear screw 52, so that axial rotation of the worm gear screw 52 translates axial rotation to the worm gear 50.

The proximal half joint 30 includes, on its underside, a projecting tab, or stop 54 (the stop lies on a center-line projecting toward the pivot point of the hinge assembly 14). The stop 54 cooperates with a tab 56 radially extending from a perimeter of a circular portion of the distal half joint 32. The stop 54 bears against, or interlocks with, the radially extending tab 56 to prevent hyperextension of the knee when pivoting from a flexion to extension positions (i.e., the stop 54 interlocks with, or bears against, the radially extending tab 56 when the upper member is 180° relative to the lower member). The distal half joint 32 includes an angled shoulder 58 that aligns with, and bears against, a rear edge 60 of the proximal half joint 30, serving as a stop to rotational movement in a flexion direction, and thereby defining a maximum extent of flexion for the hinge assembly 14, occurring when approximately 60° exists between the upper and the lower members 15, 16.

Figure 6A:
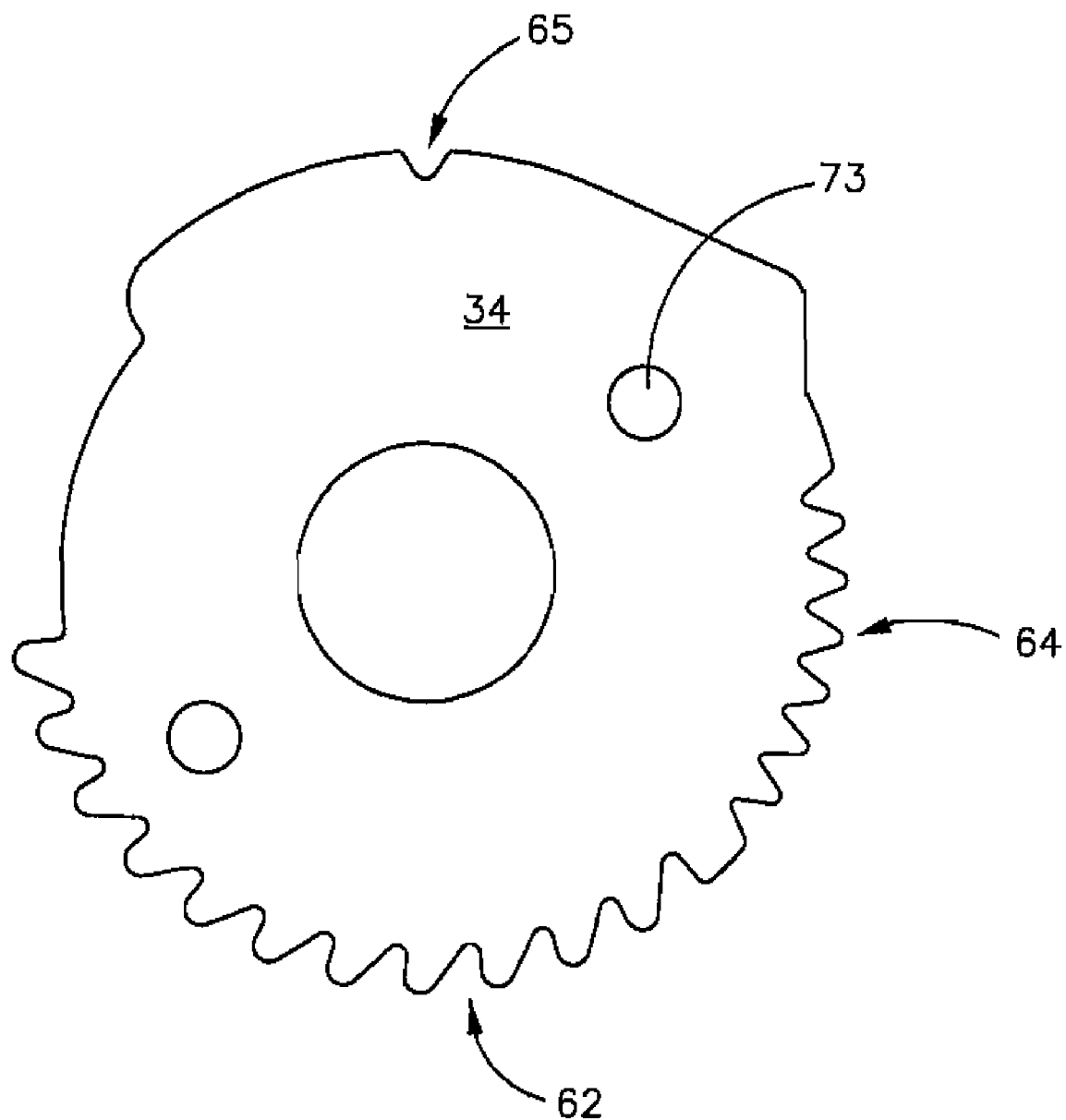
FIG. 6a illustrates the ROM disk of the previous figures, showing worm teeth and the spur teeth located about a perimeter of the ROM disk in a similar plane, FIG. 6a also showing two holes adapted to accept the spring posts.

The ROM disk 34 includes a plurality of spur teeth 62 and a plurality of worm teeth 64 about its perimeter, each lying in a similar plane. The spur teeth 62 each geometrically complement, and are selectably engagable with, the one or more slide teeth 48. Engagement of the spur teeth 62 with the slide teeth 48 work to interlock the lock slide 44 with the ROM disk 34 to arrest rotational motion of the lower member 16 relative to the upper member 15 in a direction of flexion, and enables a one-way step-advance ratcheting in a direction from flexion to extension. The spur teeth 62 are raked, or inclined, as specifically shown in FIG. 6a, to geometrically hold the interlocked spur teeth 62 and the slide teeth 48 together upon knee buckling, as when a user falls back. The weight of a user falling back, causing rotation toward flexion, ramps the spur teeth 62 and the slide teeth 48 together. Due to the incline of the respective teeth, the weight of the user acts to further interlock the geometrically complementing teeth due to the angle of incline.

The worm teeth 64 are engagably positioned with the worm gear 50 so that operation of the worm gear 50 (turning the worm gear 50 about its longitudinal axis) incrementally engages worm teeth 64 to rotate the ROM disk 34 about its axis, thereby adjusting a range of motion upon which the elastomeric spring dampening system will operate to cushion weight-bearing shock during walking and to assist leg extension during the swing phase of gait. In this embodiment, the range of motion is adjustable between approximately 0-30° about the pivot post 40.

The distal half joint 32 further includes indicating teeth 63 which cooperate with a recess 65 in the ROM disk 34 to provide simple indication of the range of motion set by operation of the worm gear 50. As the ROM disk 34 rotates about the pivot post 40, by operation of the worm gear 50, to adjust the range of motion, adjacent alignment of the recess 65 with a certain indicating tooth 63 would provide indication of a certain degree of range of motion set. For instance, in the embodiment shown in FIGS. 3*a* and 3*b*, each of four indicating teeth 63 would indicate a 10° change in range of motion (i.e., 0°, 10°, 20°, 30°). This feature is helpful to ensuring that the range of motion set for a lateral hinge assembly 12, for instance, is the same as that set for a corresponding medial hinge assembly 13.

The spring housing 38 includes two convex, cylindrically shaped channels 66, each channel 66 housing an elastomeric spring 36. In this embodiment, each elastomeric spring 36 is a cylinder of urethane. However, other elastomeric materials can be employed, such as but not limited to silicon, silicone urethane, nylon, and delrine. Depending on the dampening and urging application, various elastomeric materials, with properties ranging from elastic to inelastic, having varying degrees of rate of return to original shape or hysteresis, might be desired. The urethane springs can each be selectively designed, in size, shape and composition, to provide a pre-determined force deflection curve to match desired shock absorption characteristics, and/or to provide a pre-determined hysteresis to alter the rate of return of the elastomeric material to original (i.e., at rest, or no load) shape, to match desired swing assist and cadence characteristics, as discussed below.

Figure 5A:
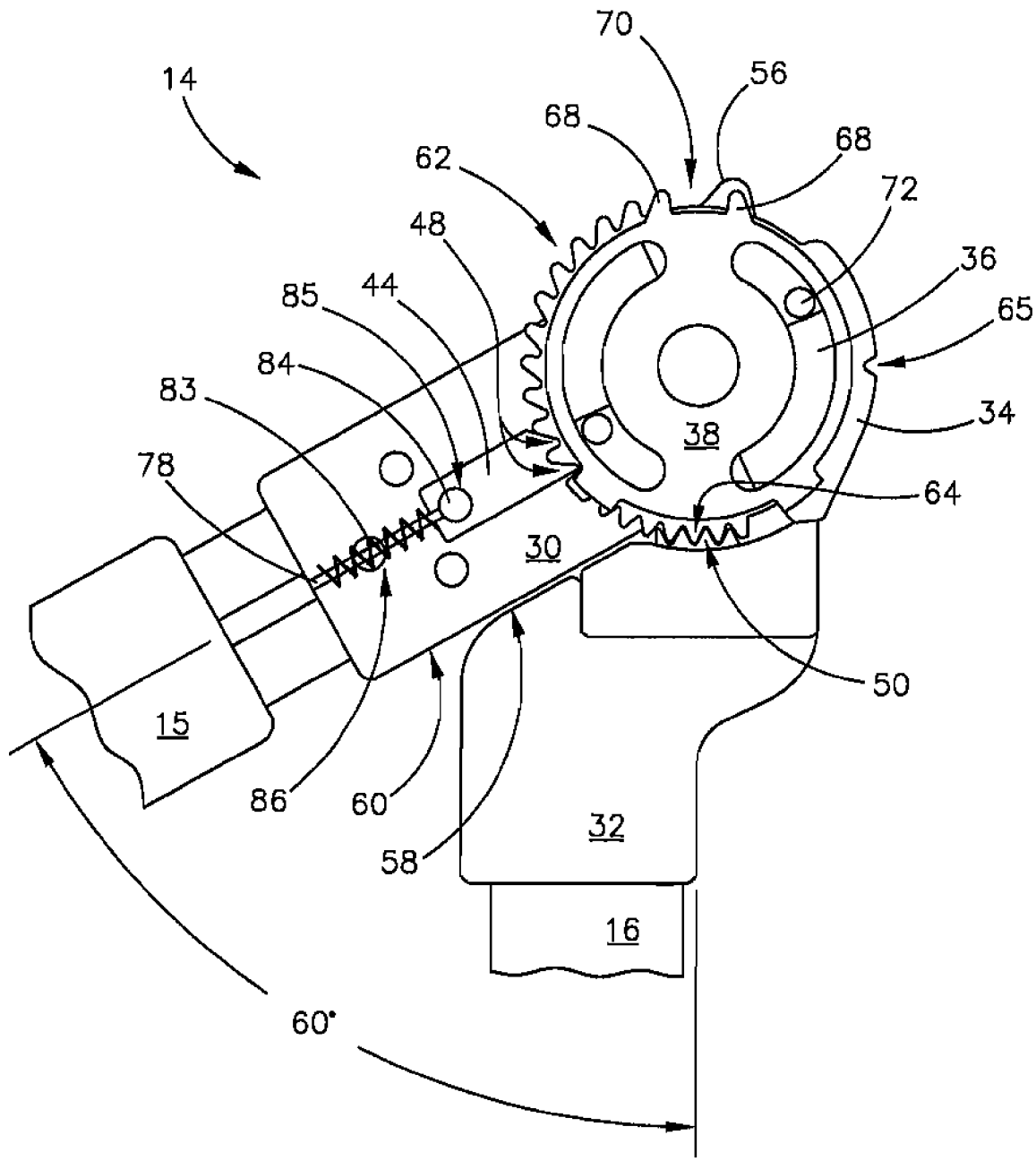
FIG. 5a illustrates a front elevation view of the hinge assembly of FIG. 1 in a position of full flexion, with slide teeth of a lock slide engaging spur teeth of a range of motion (ROM) disk to provide one-way, step advance ratcheting of rotational movement toward extension, FIG. 5a also illustrating the ROM disk set for a 30° range of motion, with elastomeric springs partially compressed (providing pre-load) due to spring post positioning within respective channels.

The spring housing 38 includes two radially extending tabs 68, forming a catch 70 therebetween, to receive the lock slide 44 upon full extension of the hinge assembly 14, thereby enabling dampening upon subsequent flexion of the hinge assembly 14, and enabling assistance upon extension. The ROM disk 34 includes two spring manipulating posts 72, each housed within a post hole 73 in, and perpendicularly extending from an outer face of, the ROM disk 34. Each spring post 72 is positioned for reception by one of the channels 66 of the spring housing 38, as shown in FIG. 5*a*, and for bearing engagement with an end of a respective elastomeric spring 36. When the lock slide 44 is secured within the catch 70, the spring housing 38 becomes rotatable relative to the ROM disk 34, so that a subsequent flexion of the hinge assembly 14 causes each spring post 72 to compress a respective elastomeric spring 36 within the respective channel 66, and against the channel 66 and the ROM disk 34. As flexion of the hinge assembly 14 increases (i.e., the upper member 15 moves toward the lower member 16), the portion of the channel 66 housing the respective elastomeric spring 36 decreases in area (due to spring housing 38 movement relative to the spring post 72), causing ever increasing confinement of the respective elastomeric spring 36. The elastomeric springs 36, during compression, provide resistance to, or dampening of, flexion of the hinge assembly 14, thereby providing the shock absorption feature of the knee brace 10 upon heel strike and weight bearing transfer during walking. Consequently, removal of weight from the flexed limb results in a decompressive force of the elastomeric springs 38 upon the spring posts 72 of the spring housing 38, which thereby urges, or assists, knee movement during the swing phase of gait from a flexion to an extension position. When the lock slide 44 is not secured within the catch 70, the flexion restraint and extension assistance features are disengaged, as rotatable movement of the spring housing 38 relative to the ROM disk 34 is avoided.

Figure 4A:
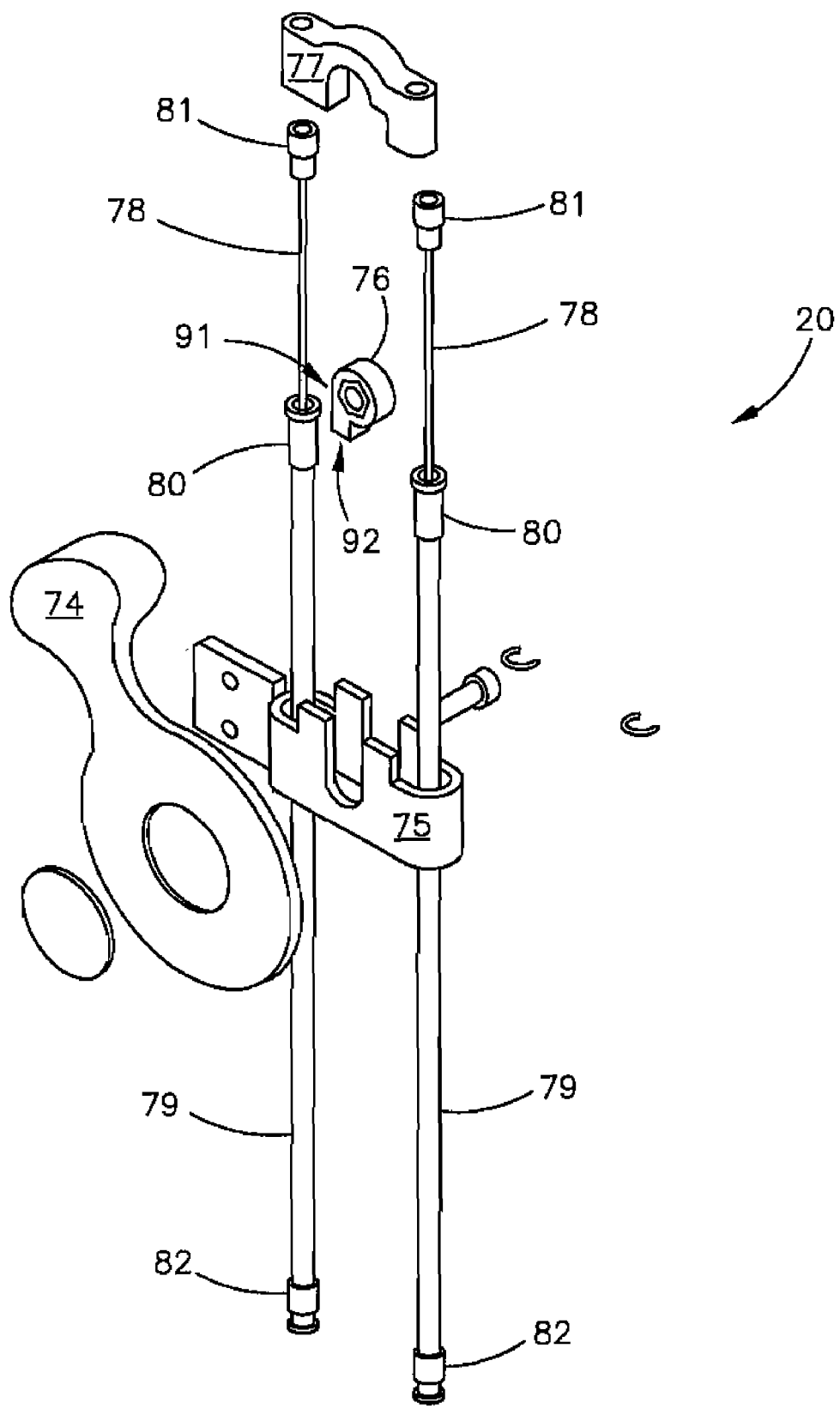
FIG. 4a illustrates a front-side, perspective, exploded view of a cable release mechanism in accordance with one embodiment of the present invention.
Figure 4B:
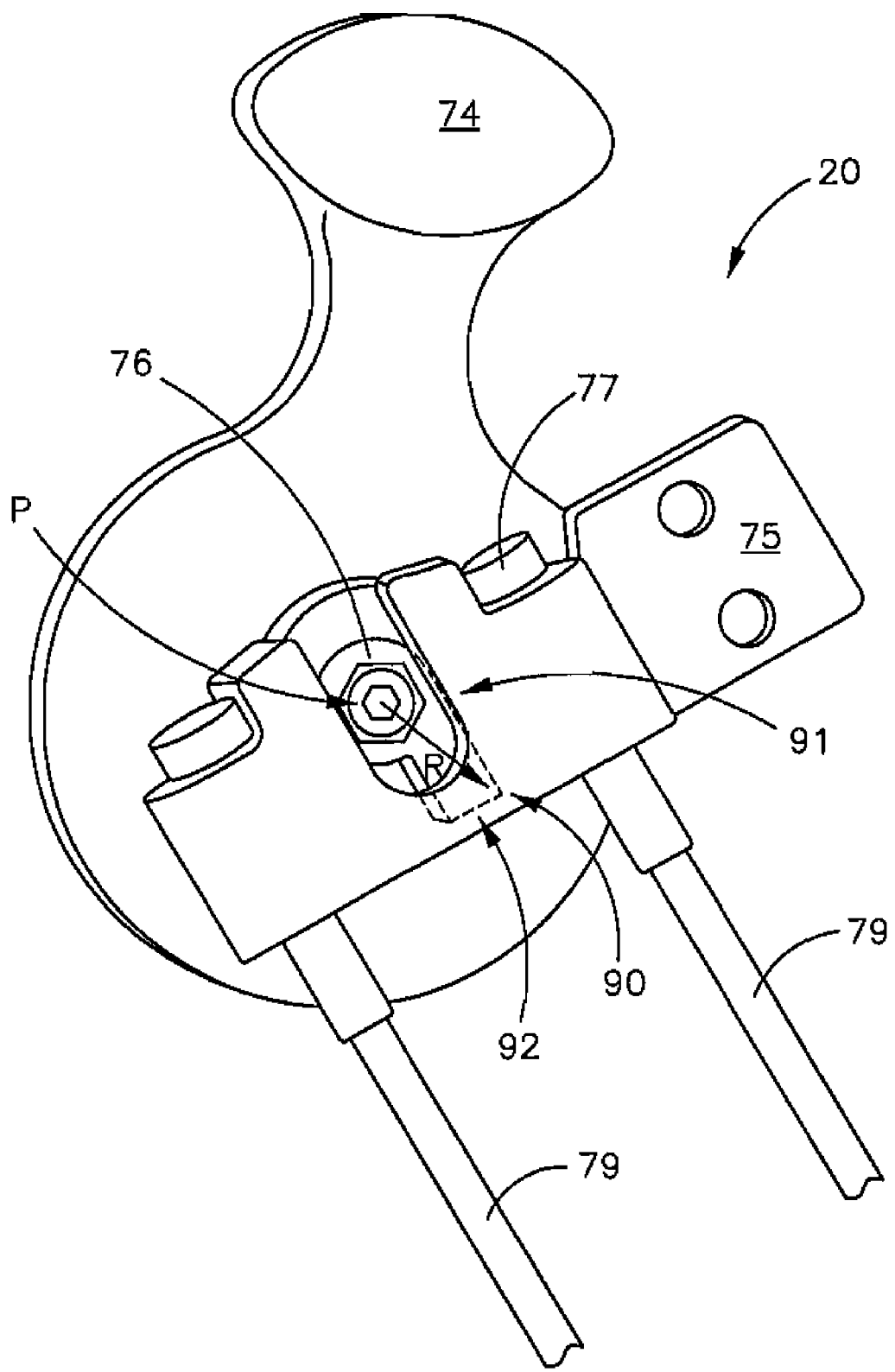

Referring now to FIGS. 4*a* and 4*b*, the cable release mechanism 20 of associated lock slide assembly 18 includes a lever 74, a cable release housing 75, a toggle cam 76, a cable slide 77, and two cables 78. The two cables 78 are each retained within a tube 79, each tube 79 having on its proximal end a housing fitting 80 which cooperates with a threaded terminal 81 on each cable 78 end to retain the cable slide 77 within a recess in the housing 75. Each of the two cables 78 operate a respective lock slide assembly 18 (one serving the lateral joint assembly 12 and the other serving the medial joint assembly 13).

Referring now to FIGS. 3*a*, 4*a*, and 4*b*, each tube 79 has on its distal end a lock slide end fitting 82 which cooperates with the proximal half joint 30 to terminate the cable release mechanism 20 at the lock slide assembly 18. A bulbous cable fitting 83, at a distal end of the cable 78, resides within a circular recess 84 in the lock slide 44. The cable 78 passes through the distal biasing spring 85 residing within a spring recess 86 in the proximal half joint 30. The lock slide end fitting 82 is nestled and secured within a detent 87 formed within the proximal half joint 30 and the lock slide cover 48 upon attachment of the lock slide cover 48 to the proximal half joint 30. The distal biasing spring 85 predisposes the slide teeth 48 of the lock slide 44 into engagement with the spur teeth 62 of the ROM disk 34, or predisposes the lock slide 44 into engagement with the catch 70 of the spring housing 38, depending on the position (flexion or extension) of the lower member 16 (or distal half joint 32) relative to the upper member 15 (or proximal half joint 30). Pulling the cables 78 compresses the distal biasing spring 85 and retracts the lock slide 44, thereby translating the lock slide 44 away from the pivot point and disengaging the lock slide 44 from either the spur teeth 62 of the ROM disk 34 or the catch 70 of the spring housing 38. When the lock slide 44 is disengaged from the spring housing 38 and the ROM disk 34, the lower member 16 rotates freely relative to the upper member 15 about the pivot point within a range of approximately 120°.

Referring now to FIGS. 2, 4*a*, and 4*b*, at a proximal end of the upper member 15, the cable release housing 75 is fixedly attached to the upper member with setscrews. The lever 74 is fixedly secured to the toggle cam 76 by retaining screw 88. The toggle cam 76 is rotatably and translatably housed within the recess in the cable release housing 75, being retained therein by the cable slide 77 biased to retain the toggle cam 76 within the housing 75 by taut cables 78.

The toggle cam 76 is designed with a projecting cammed surface 90, a first flat surface 91, and a second flat surface 92, the cammed surface 90 bearing against a bottom 75 of the recess in the cable release housing 75. When the lever 74 is pivoted about the retaining screw 88 (at pivot point "P"). The projecting cammed surface 90, bearing against the bottom 75 of the recess in the cable release housing 75, causes the retaining screw 88 and cable slide 77 to translate linearly within the recess of the cable release housing 75 a sufficient distance so that the cables 78 retract the respective lock slides 44, disengaging the lock slides 44 from the respective spring housings 38 or ROM disks 34 of the medial and the lateral hinge assemblies 14. The projecting cammed surface 90 incorporates a radius "R" (relative to the pivot point P) greater than that of distances to either of the first or the second flat surfaces 91, 92, which causes a toggle action and snap, under cable tension, when moving from a cammed surface 90 engagement with the bottom 93 to either a first or a second flat surface 91, 92 engagement with the bottom 93, thereby providing a user with a positive and certain positioning (engagement or disengagement) of the lock slide assembly 18 for each of the lateral and medial joint assemblies 12, 13.

Accordingly, each cable 78, when positioned in retraction, independently exerts a force greater than that of the corresponding distal biasing spring 85 to assure a force necessary to fully disengage the lock slide 44. The toggle cam 76, due to the cammed surface 90, linearly translates the cables 78 a distance greater than that necessary to disengage the lock slide 44 from each hinge assembly 14, and does so without over-tensioning the respective cable 78. Additional components that can be employed to assist in preventing cable over-tensioning are detailed later in a description of another embodiment of a cable release mechanism.

When the lever 74 is "raked" up (as shown in FIGS. 4a and 4b), the second flat surface 92 (with distance to the pivot point P greater than that of the first flat surface 91) is adapted to hold the cable in a "proximally pulled" position to hold the lock slide 44 in a fully disengaged position relative to the ROM disk 34 and the spring housing 38. When the lever 74 is "knuckled" down, relative to the patient, the first flat surface 91 (with distance to the pivot point P less than that of the second flat surface 92) is adapted to enable a more distal positioning of the tensioned cables 78, permitting the lock slide 44 to remain in a fully engaged position relative to the ROM disk 34 or the spring housing 38.

An Operating Description of the Exemplary Embodiment

FIGS. 5a-5e illustrate the hinge assembly 14 of the knee brace 10 in various positions of use, each position employing one or more features of the present invention. FIG. 5a illustrates the hinge assembly 14 in a position of full flexion, with the angled shoulder 58 of the distal half joint 32 bearing against the rear edge 60 of the proximal half joint 30, the bearing relationship serving as a stop to rotational movement in a flexion direction. At full flexion, approximately 60° exist between the upper and the lower members 15, 16. Accordingly, approximately 120° defines a complete range of motion between full flexion and full extension.

FIG. 5a shows the lock slide 44 engaging respective spur teeth 62 of the ROM disk 34, thereby enabling sit-to-stand support, for users having difficulty rising from a sitting position, through one-way, step-advance ratcheting. As shown in FIG. 5a, rotational movement toward extension causes the slide teeth 48 to incrementally advance, and ratchet, over the spur teeth 62 of the ROM disk 34. This one-way, step advance ratcheting allows controlled knee extension while preventing knee buckling. If a knee begins a flexing movement (i.e., begins buckling) before reaching full extension, the slide teeth 48 engage with and lock into the spur teeth 62. Upon full extension, the slide teeth 48 disengage from, and move out of the vicinity of, the spur teeth 62.

Figure 5B:
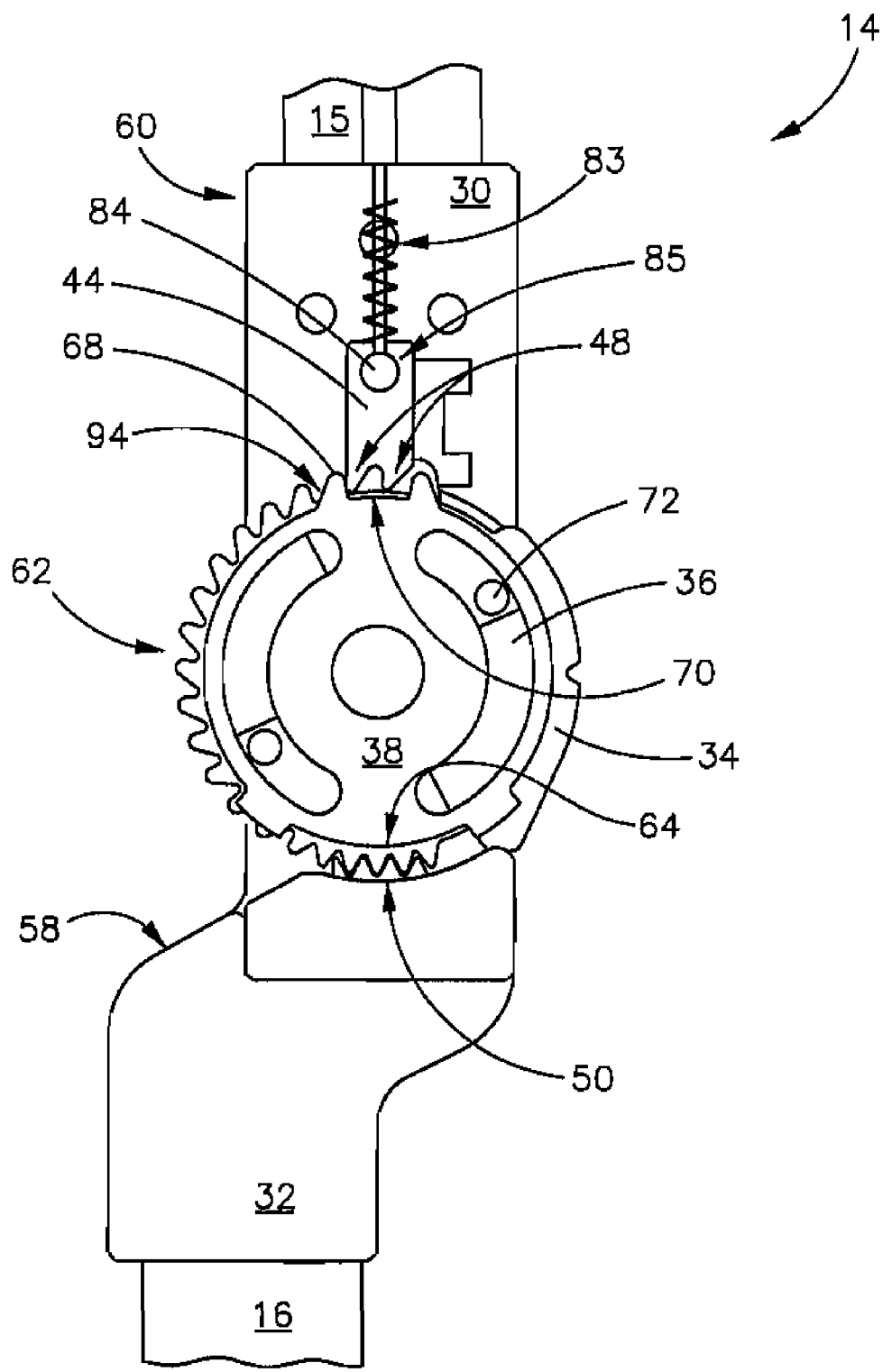
FIG. 5b illustrates a front elevation view of the hinge assembly of FIG. 1 in a position of full extension, with the slide teeth engaging a catch in a spring housing and the ROM disk set for a 0° range of motion (i.e., the slide teeth abut a proximal most spur, tooth of the ROM disk, the abutment arresting rotational movement toward flexion)
Figure 5C:
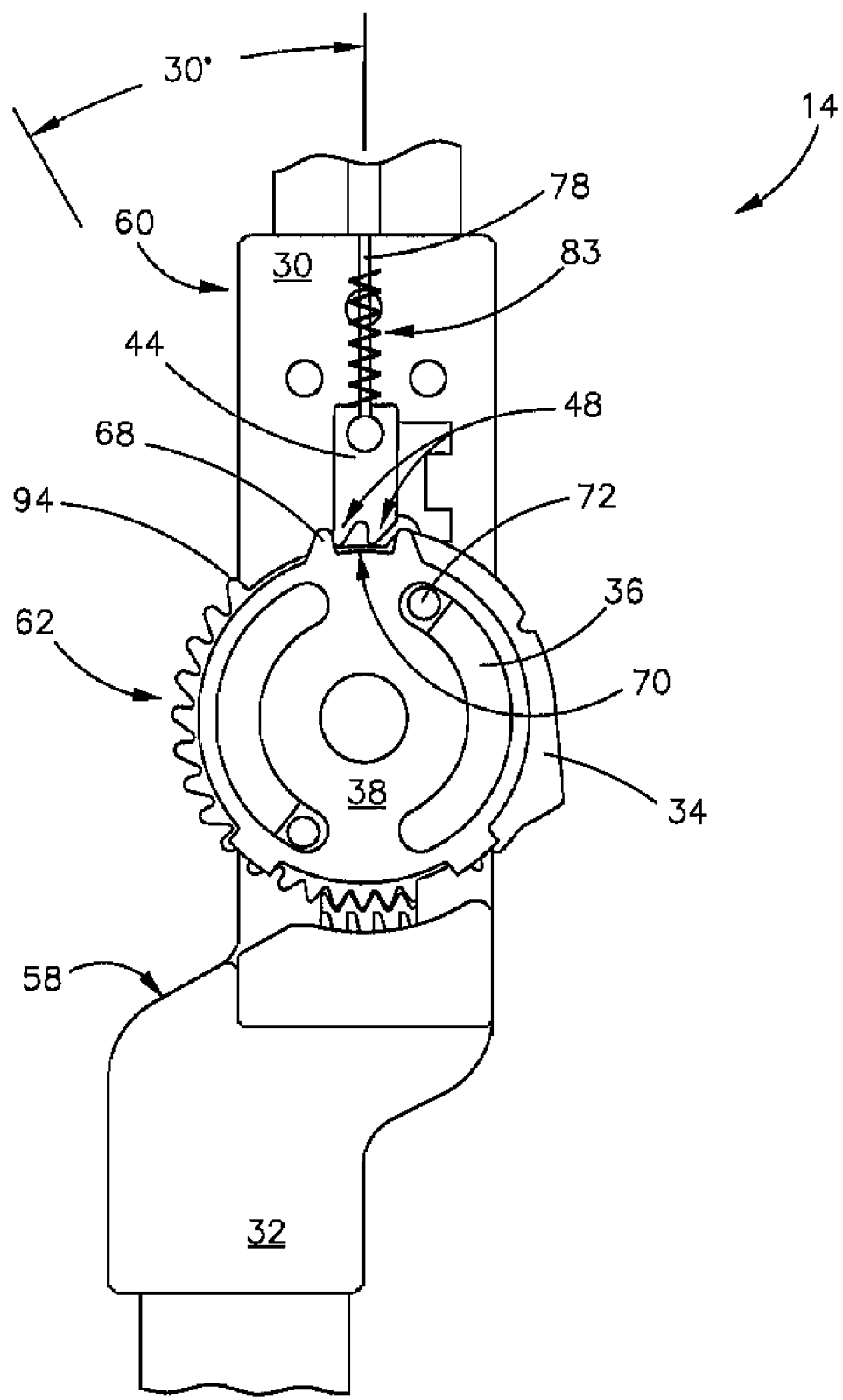
FIG. 5e illustrates a front elevation view of the hinge assembly of FIG. 1 in a position of full extension, with the slide teeth engaging the catch in the spring housing and the ROM disk set for a 30° range of motion, thereby enabling, within the 30° range of motion, a dampening of rotation toward flexion and an urging of rotation toward extension.
FIG. 5d illustrates a front elevation view of the hinge assembly of FIG. 1 in a position maximizing the 30° range of motion, FIG. 5d showing springs compressed and dampening the rotation toward flexion.

FIG. 5b illustrates the hinge assembly 14 in a position of full extension, with the lock slide 44 secured within the catch 70 of the spring housing 38. Although engaged within the catch 70, the lock slide 44 (as shown in FIG. 5b) still abuts a proximal most spur tooth 94 located about a perimeter of the ROM disk 34. The proximal most spur tooth 94 is shown in FIG. 5b partially behind a rearmost radially extending tab 68 (rearmost because FIG. 5b is a view of a right handed, lateral hinge assembly 14). In this position, at least one slide tooth 48 of the lock slide 44 will bear against the proximal most spur tooth 94 during any attempted movement toward flexion. The hinge assembly 14, therefore, is locked at full extension. Accordingly, FIG. 5b shows the ROM disk 34 positioned to allow a 0° range of motion, the range of motion being by operation of the worm gear 50. As such, the knee is locked at full extension, giving the user stability in stance, a confidence of not falling due to knee buckling, but requiring the user to walk with a stiff knee and consequential strutting gait. A 0° range of motion might be used by a stroke patient during early stages of rehabilitation, when confidence and strength may be lacking.

Figure 5D:
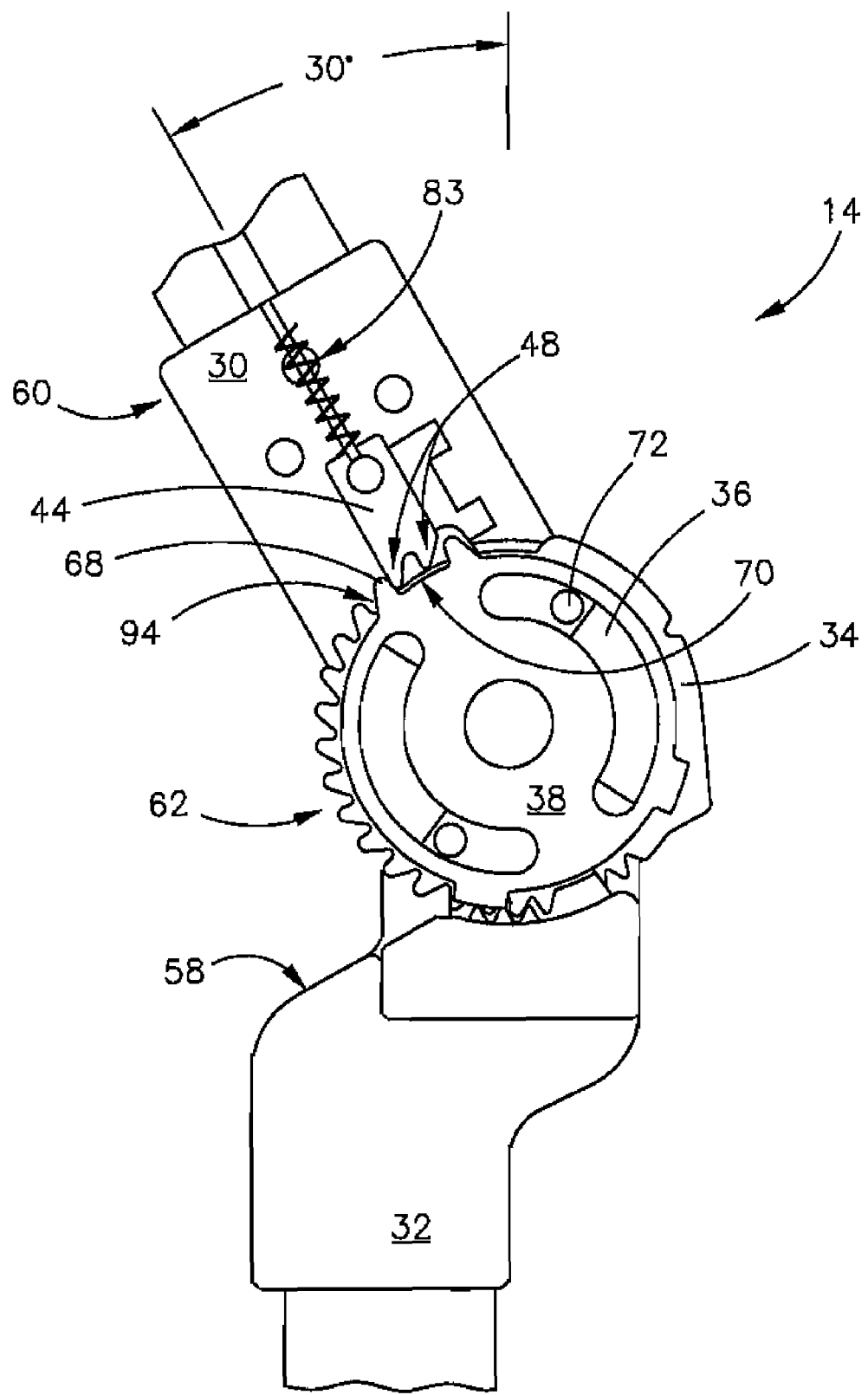
Figure 5E:
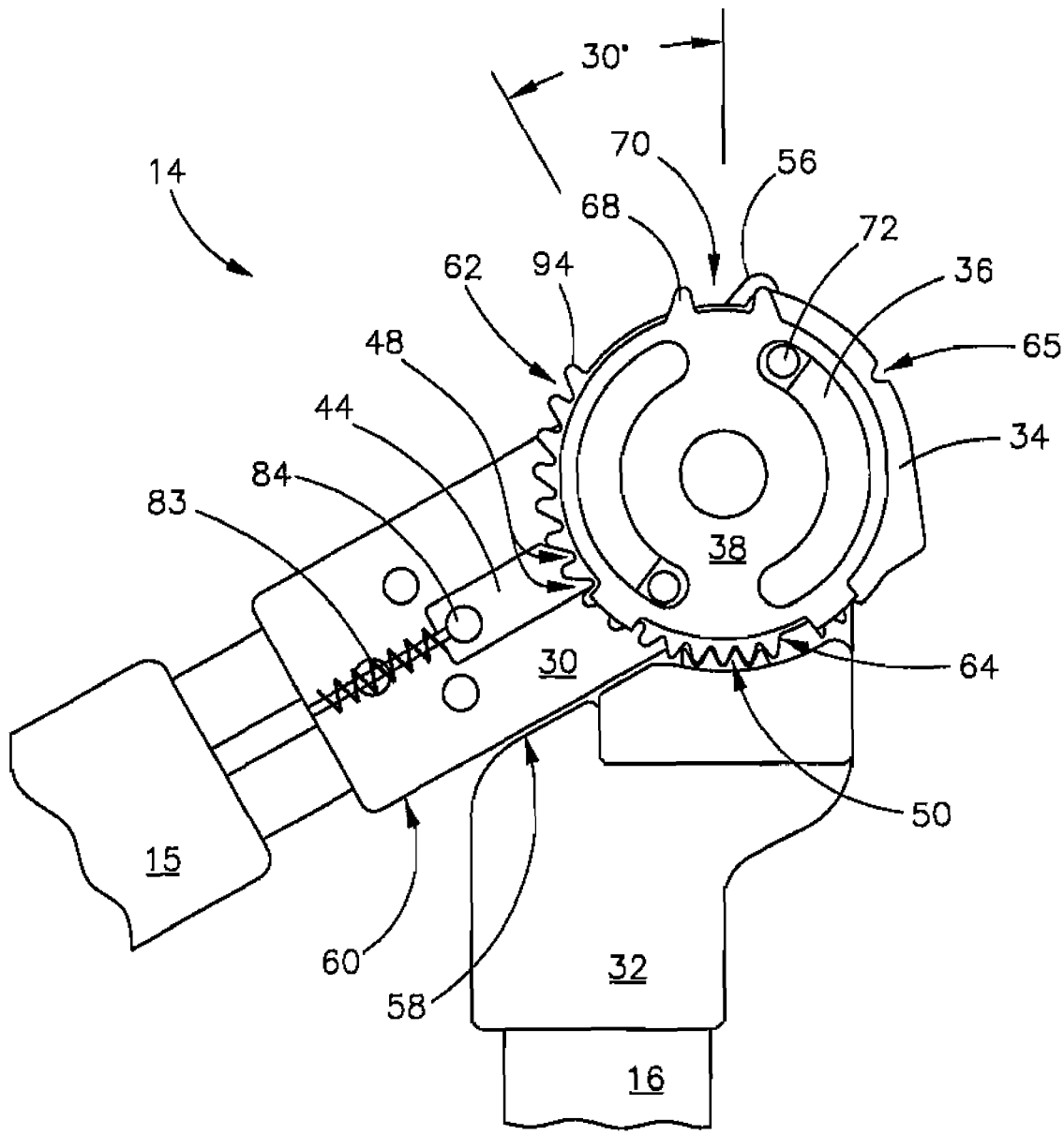

FIG. 5e illustrates the hinge assembly 14 in a position of full extension, the lock slide 44 secured within the catch 70 of the spring housing 38, and the ROM disk 34 positioned to allow a 30° range of motion, as set by operation of the worm gear 50, and as shown by the locational relationship between the proximal most spur tooth 94 and the rearmost radially extending tab 68. Within the 30° range of motion, with the lock slide 44 secured within the catch 70, movement toward flexion causes the spring housing 38 to rotate in conjunction with the proximal half joint 30, about the pivot post 40, and to rotate relative to the ROM disk 34 so that each spring post 72, during movement toward flexion, compresses a respective elastomeric spring 36 within and against the respective channel 66 and against the ROM disk 34.

FIG. 5d illustrates the hinge assembly 14 with the lock slide 44 secured within the catch 70, the ROM disk 34 positioned to allow a 30° range of motion, and the elastomeric spring 36 flexion dampening/extension assisting mechanism engaged, FIG. 5d shows the hinge assembly 14 reaching a maximum point within the 30° range of motion, at which point the lock slide 44 will abut the proximal most spur tooth 94 to arrest further flexion, and thereby prevent knee buckling and a possible fall if the user's knee were to fail. FIG. 5d shows the elastomeric springs 36 compressed within respective channels 66 to restrain flexion, to provide dynamic shock absorption at initial contact (i.e. at heel strike through midstance), and to dampen ground reaction forces and loading responses to redirect forces to propel forward progression for greater efficiency for smoother knee flexion during gait. Thereafter, a release of weight bearing force to the hinge assembly 14 causes the compressed elastomeric springs 36 to urge the upper and the lower members 15, 16 back toward extension, thereby assisting the user in achieving full terminal swing in the presence of extensor weakness, and to ensure that the heel hits the ground first (rather than the mid or forefoot) at initial strike. The elastomeric springs 36 can be varied in size, type, and shape, as discussed below, to provide a wide range of force deflection curves, thereby allowing the present invention to mimic a wide variety of desirable muscle responses, and/or to provide varying restraint of flexion and assistance to extension at different points along the range of motion.

At any point during operation, proximally translating the cable 78 (i.e., "raking" up the lever 74) disengages the lock slide 44 from the spring housing 38 to allow free rotation of die upper member 15 relative to the lower member 16. Disengaging the look slide 44 permits flexion beyond the 30° range of motion, to a desired sitting position, up to and including a position of full flexion. At full flexion, "knuckling" the lever 74 down again engages the lock slide 44 with the ROM disk 34 to again enable the one-way step advance feature, as shown in FIG. 5e. FIG. 5e further shows the ROM disk 34 positioned to allow a 30° range of motion, and the elastomeric springs 36 relaxed, with the flexion dampening/extension assisting mechanism disengaged.

Exemplary Embodiments of the Elastomeric Springs

The elastomeric springs 36 are Compressed within the channels 66 by the spring posts 72 of the ROM disk 34. The spring posts 72 move within the channels 66, each bearing against one end of an elastomeric spring 36, to translate a non-linear compressing force through the spring 36 beginning at the end. Upon compression, the elastomeric cylinders decrease in length and expand in diameter to frictionally embrace the inner walls of the channels 66 and an outer face of the ROM disk 34. Accordingly, varying the properties of the elastomeric springs 36, and/or varying the characteristics of the frictional embrace of the springs 36 to the channels 66 and the ROM disk 34, can control the force deflection and rate of return response of the elastomeric spring 36.

In one embodiment, the outer diameter of the elastomeric springs is less, or slightly less, than an inner diameter of the channels. In this embodiment, a shape of the inner walls could approximate an exterior of the springs, or could vary to some degree, depending on a deflection response desired. In either case, in this embodiment, the spring diameter must expand to some degree, through compression of length, before the spring will frictionally embrace the inner walls of the channel and the ROM disk. In another embodiment, the outer diameter of the spring might be substantially equal (in shape and diameter) to the inner wall of the channel, thereby creating a higher coefficient of friction to immediately absorb more energy.

In another embodiment, the elastomeric spring might have a hole bored longitudinally therethrough, the hole affecting expansion of the spring diameter during compression, as the spring material must now expand to fill the hole, the hole thereby consequently affecting the coefficient of friction of the spring. The longitudinal hole, and a varying of the diameter of the hole, could be used with either of the spring diameter configurations described above.

In another embodiment, a setscrew or pin is placed in a pre-determined location within the channels to stiffen the dampening response. Since a channel with less surface area (as determined by a position of the setscrew or pin) provides the elastomeric spring less room to expand, the elastomeric spring will become uncompressible sooner, thereby increasing resistance to flexion.

Figure 6B:
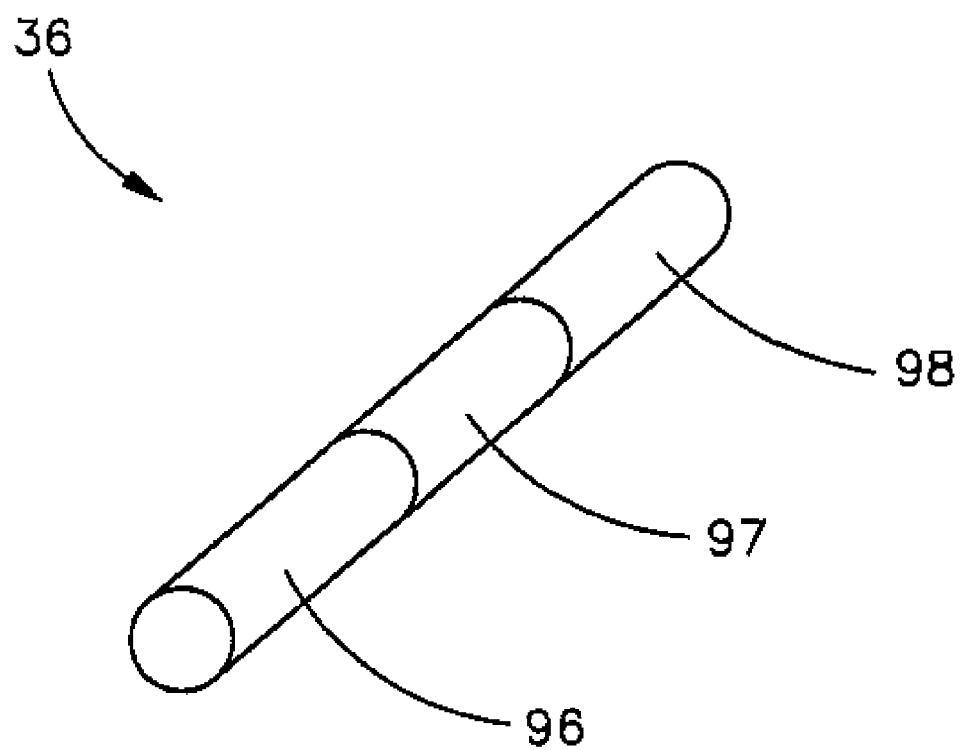
FIG. 6b illustrates one embodiment of an elastomeric spring in accordance with the present invention.

In another embodiment, the cylindrical elastomeric spring 36 is longitudinally segmented with portions of differing durameters, or densities, to vary the restraining force and rate of return over the range of motion of the hinge assembly. Referring now to FIG. 6b, an elastomeric spring 36 is illustrated having three segments, each segment having a different density to impart a certain desired force deflection curve over a respective portion of the range of motion. For example, a first segment 96 may have a relatively low durameter, with corresponding high elasticity, thereby providing a light moment of lesser shock absorption, but providing a rate of return, or extension assistance, typical of a normal swing of gait. The second segment 97 may be of moderate durameter, with corresponding moderate elasticity, thereby providing a greater restraining force and shock absorption, but providing a lesser rate of return. The third segment 98 might include dense material, of high durameter and low elasticity, thereby enabling absorption of greater force, but providing a slower return and consequently not providing a lot of swing assist.

In the above-segmented embodiment of the elastomeric spring 96, the first segment 96, due to its position bearing against the spring post 72, is the first to operate, or acquire compressive forces, during flexion restraint, and the last to operate, or decompress, during extension assistance. For this reason, a material with high elasticity and low durameter may be desirable, to ensure a certain degree of flexion during heel strike and loading response, while providing a high rate of return, or swing assist, to ensure proper heel strike (i.e., to ensure that the heel strikes the ground first) over the final portion, or range, of swing. Since the third segment 98 is the last portion of the elastomeric spring 36 to sustain compressive forces, and offer flexion restraint, over the range of motion during flexion, it may also be desirable to design the third segment 98 of dense material, with high durameter, to provide a high level of shock absorption, or flexion restraint, over this final portion of flexion to avoid a "maxing out" of the joint assembly (i.e., to avoid a complete arresting of flexion upon reaching the maximum range of motion set point (e.g., 30°)) during heel strike and weight transfer.

The hysteresis characteristic of elastomeric materials makes elastomeric materials favorable for employment in the present invention. With elastomeric materials, greater shock absorption, or flexion restraint, in compression does not necessarily result in an equally great rate of return, or swing assist, in decompression. Elastomeric materials return slower, in decompression, than correspondingly respond to a force in compression. This characteristic resembles bodily musculature, where, for instance, a quadricep during heel strike and stance absorbs, or resists, a greater force than the quadricep subsequently returns during the swing phase of gait. This feature makes elastomeric springs advantageous to torsion springs, which return quickly, where a spring loaded to absorb a significant force will subsequently return with swing assist far exceeding that needed or desired by a user. Accordingly, a time rate of compression of an elastomeric spring in response to a certain force is faster than a subsequent time rate of decompression of the elastomeric spring resulting from the certain force. Further, as a result, an elastomeric spring of the present invention can be adapted to provide a pre-determined force deflection curve in compression, and an independent rate of return hysteresis in decompression.

The above-referenced alternatives and aspects of the elastomeric springs provide many characteristic permutations, the various permutations enabling the achievement of myriad force deflection and hysteresis curves. Accordingly, any bodily tissue or muscle can be reproduced, or mimicked, by the present invention. For instance, muscle performance can be assessed in a laboratory, and a force deflection curve charted. Then, an elastomeric spring can be adapted to mimic the charted force deflection curve by selectively determining the necessary size, shape, features, and characteristics of the elastomeric spring.

Alternative Embodiments of the Hinge Assembly and Cable Release Mechanism

Figure 7A:
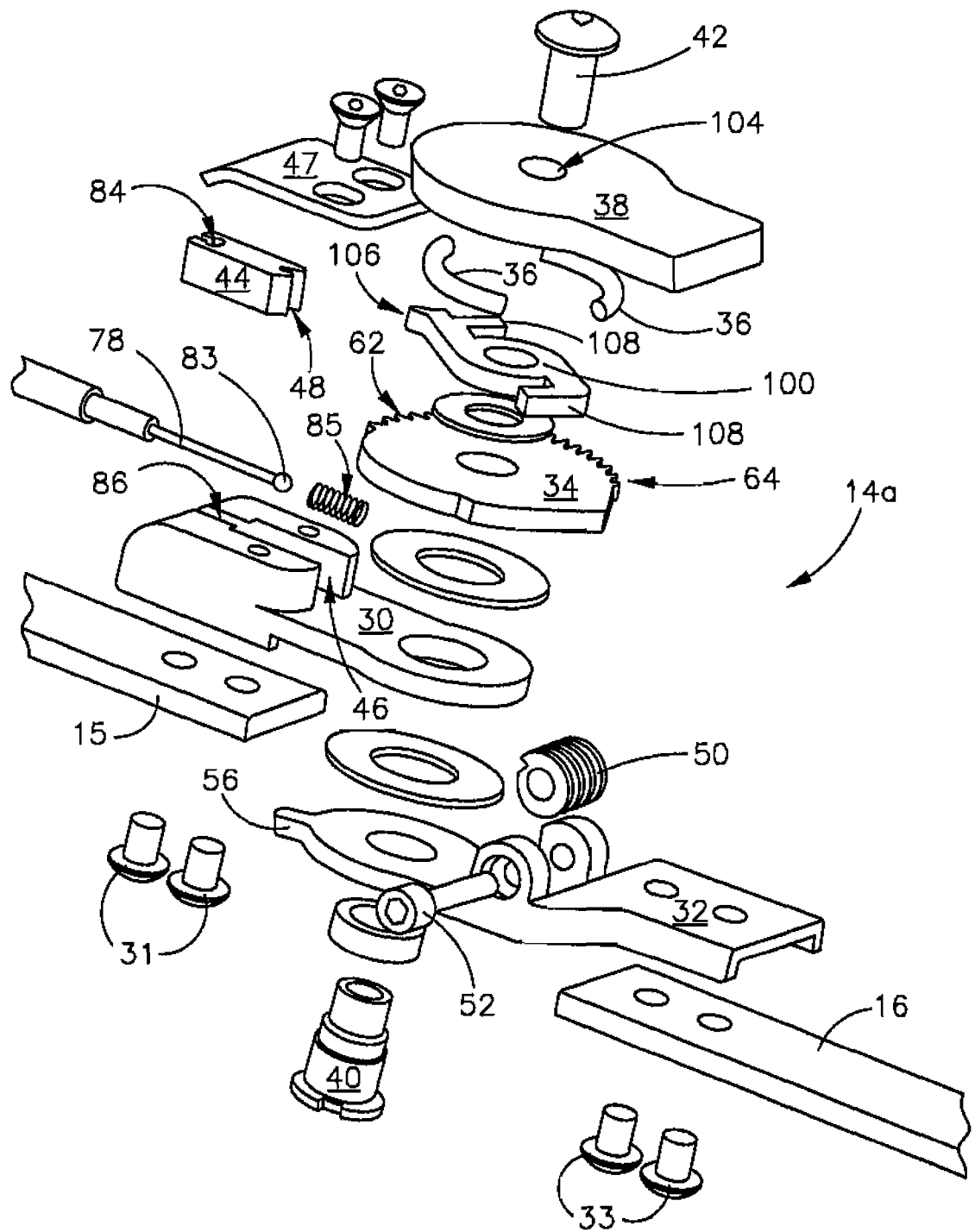
FIG. 7a illustrates an overhead, or front-side, perspective, exploded view of a lateral, left-hand alternative hinge assembly in accordance with another embodiment of the present invention.
Figure 7B:
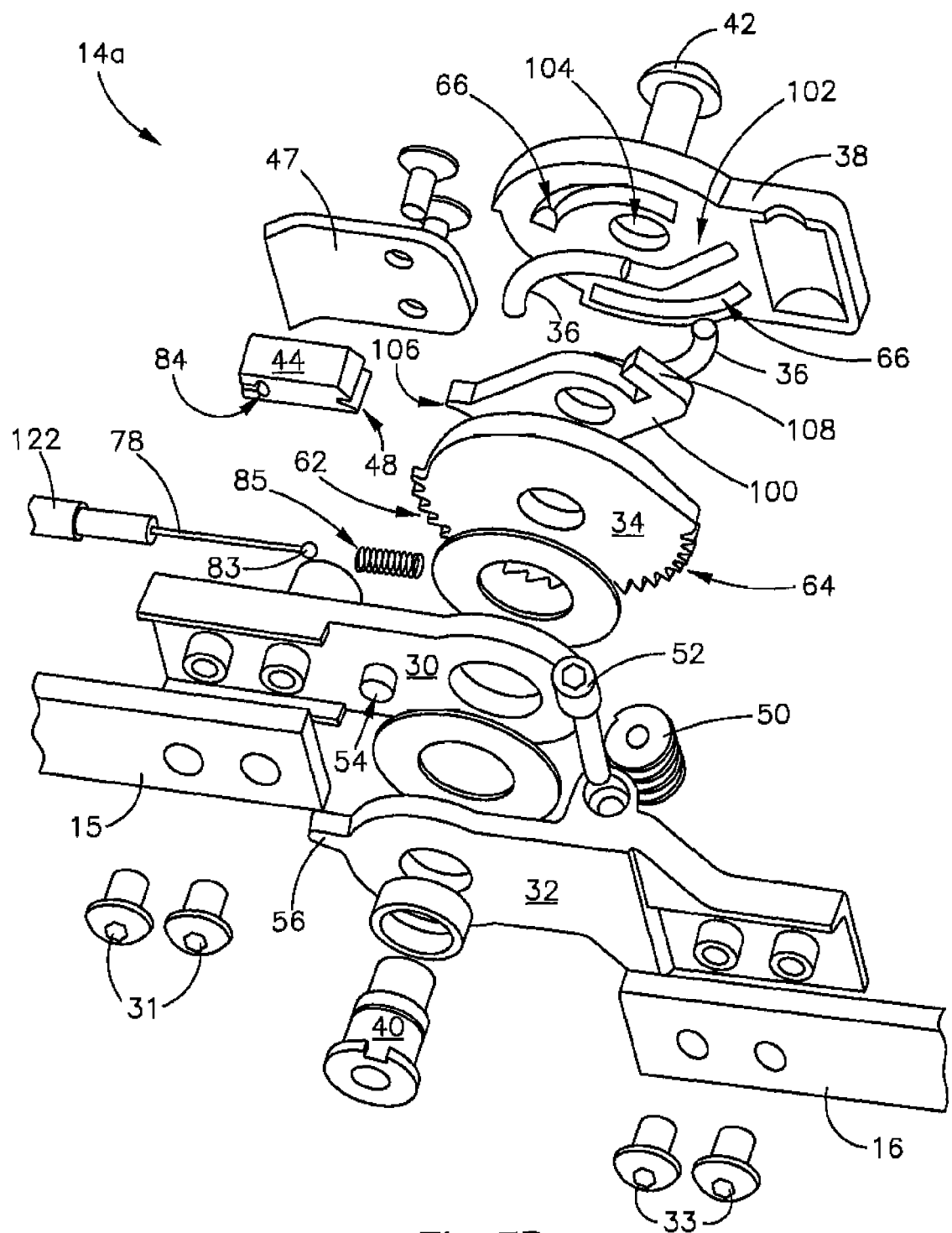

FIGS. 7a and 7b illustrate a hinge assembly 14a embodiment alternative that shown in FIGS. 3a and 3b. This latter hinge assembly 14a includes many of the same components and functionality of the hinge assembly 14 of FIGS. 3a and 3b, but does differ in at least a modified spring housing 38 and one additional component, a rotor 100, described as follows.

The spring housing 38 includes two convex, and cylindrically shaped, channels 66, each channel 66 housing an elastomeric spring 36. In this embodiment, each elastomeric spring 36 is a cylinder of urethane. Adjacent to each of the channels 66, within the spring housing 38, is a recess 102 centered about a hole 104 (through which the pivot post 40 extends) that houses the rotor 100. Within the recess 102, the rotor 100 rotates about the pivot post 40. The rotor 100 includes one or more end teeth 106, and two claws 108. The one or more end teeth 106, each geometrically complement, and are selectably engagable with, the one or more slide teeth 48. When the one or more end teeth 106 are engaged with the one or more slide teeth 48 (which occurs at full extension), rotation of the lower member 16 relative to the upper member 15 toward a flexion position causes each claw 108 of the rotor 100 to bear against a respective elastomeric spring 36 and to compress the spring 36 against its respective and confining channel 66. The elastomeric spring 36, during compression, provides resistance to the flexion of the hinge assembly 14a, and the shock absorption feature upon heel strike and weight transfer during walking. Consequently, removal of weight from a respective flexed limb results in a decompressive force of the elastomeric springs 36 upon the claws 108 of the rotor 100, which thereby urges, or assists, knee movement during the swing phase of gait from a flexion to an extension position.

Regarding the force deflection curve provided by the elastomeric springs 36, the hinge assembly 14*a* of FIGS. 7*a* and 7*b* functionally differs from the hinge assembly 14 of FIGS. 3*a* and 3*b*. Adjusting the range of motion (ROM) of hinge assembly 14*a*, through rotation of the ROM disk 34 via operation of the worm gear 50, does not effect the rotor 100 or spring housing 38 (i.e., the rotor 100 and spring housing 38 remain stationary (unaffected) by ROM adjustment). Accordingly, the claws 108 of the rotor 100 are positioned similarly, relative to a respective elastomeric spring 36, just prior to heel strike, regardless of the ROM setting.

Contrast the hinge assembly 14 of FIGS. 3*a* and 3*b*, where the spring posts 72, connected to the ROM disk 34, rotate along with the ROM disk 34 during a change to ROM setting. Accordingly, the elastomeric spring 36 may begin (i.e., just prior to heel strike) at rest (i.e., uncompressed), or may begin at various degrees of compression based upon a selected ROM setting (see FIG. 5*a*, where the spring 36 begins compressed with a 0° ROM setting, versus FIG. 5*c*, where the spring 36 begins essentially at rest with a 30° ROM setting). This difference in functionality adds to the various spring permutations, discussed above, further enabling achievement of myriad force deflection and hysteresis curves.

Figure 8:
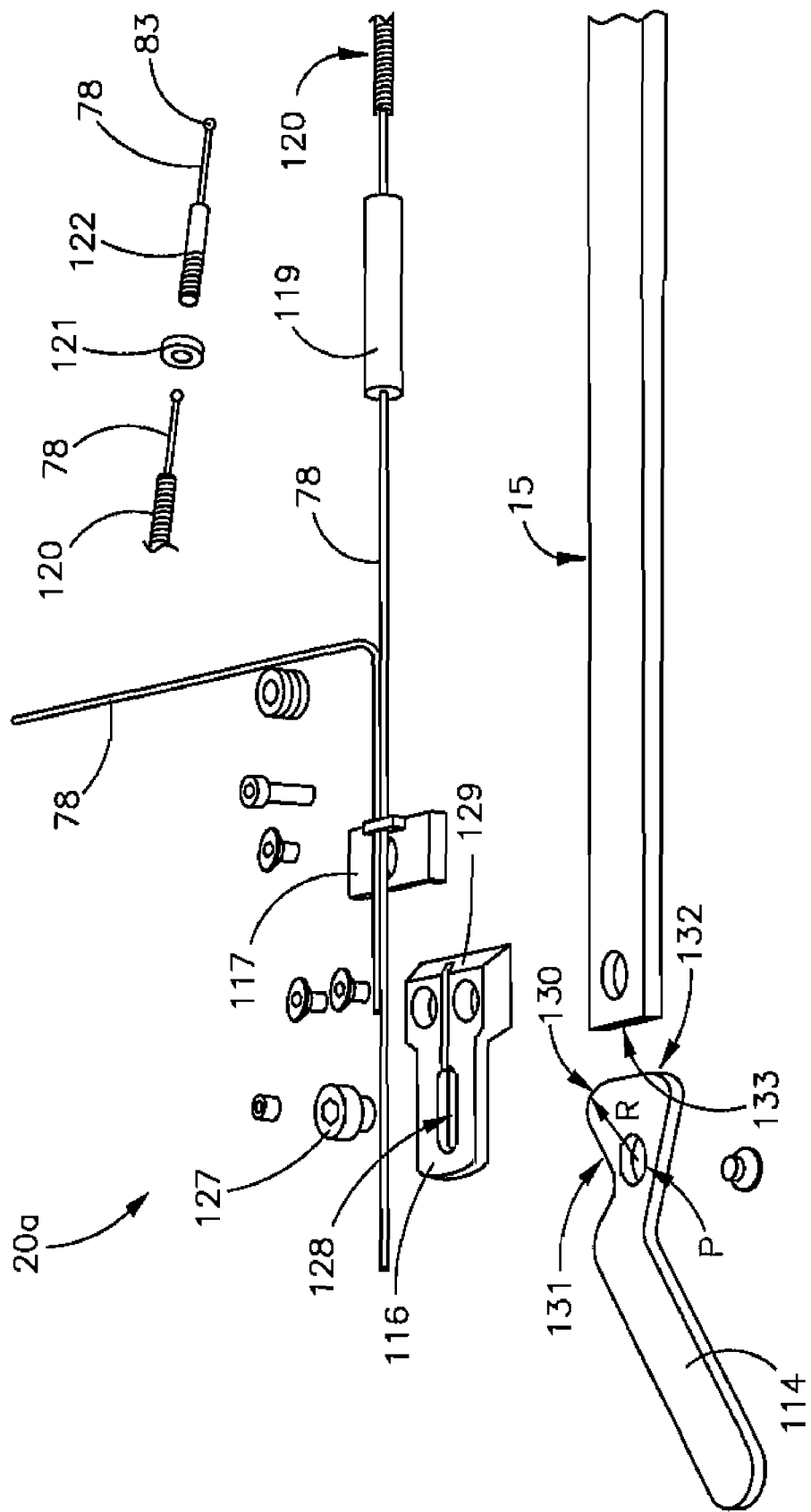
FIG. 8 illustrates a front-side, perspective, exploded view of an alternative cable release mechanism in accordance with another embodiment of the present invention.

FIG. 8 illustrates a cable release mechanism 20*a* embodiment alternative that shown in FIGS. 4*a* and 4*b*. This latter cable release mechanism 20*a* includes many of the same components and functionality of the cable release mechanism 20 of FIGS. 4*a* and 4*b*, particularly the linearity of cable 78 movement and the camming action, linearly translating the cables 78 a distance greater than that necessary to disengage the lock slide 44, without over-tensioning the respective cable 78, to provide a positive sensory and auditory feedback (snap) upon engagement, thereby ensuring the user that the cam-lock feature is fully actuated in either the engaged (locked) or disengaged (unlocked) position. This latter cable release mechanism 20*a* provides the similar functionality through differing components, or different forms of similar components, described as follows. Further, components are introduced for assisting the prevention of cable over-tensioning. The components, described herein, are equally adaptable for employment with the cable release mechanism 20 of FIGS. 4*a* and 4*b*.

The cable release mechanism 20*a* of FIG. 8 includes a lever 114, a cable lever housing 116, a cable guide 117, the two cables 78, a proximal terminal 119, a proximal compression spring 120, a locknut 121, a distal terminal 122, the distal biasing spring 85, and the bulbous cable fitting 83.

At a proximal end of the upper member 15, the cable lever housing 116 is fixedly attached to the upper member 15 with setscrews. The lever 114 is rotatably and translatably attached to the cable lever housing 116 by a binder post 127 through a slot 128 in the cable level housing 116, the binder post 127 also securing a proximal end of the cables 78, the cables 78 lying and linearly translating within groove 129 of the cable lever housing 116.

The lever 114, like the toggle cam 76, is designed with a projecting cammed surface 130, a first flat surface 131, and a second flat surface 132, the cammed surface 130 bearing against a proximal end 133 of the upper member 15 when the lever 114 is pivoted about the binder post 127 within the slot 128. The projecting cammed surface 130, bearing against the proximal end 133 of the upper member 15, causes the binder post 127 to translate linearly within the slot 128 a sufficient distance so that the cables 78 retract the respective lock slides 44, disengaging the lock slides 44 from the spring housing 38 or the ROM disk 34 of the medial and the lateral hinge assemblies 14, 14*a*. The projecting cammed surface 130 incorporates a radius R (relative to the lever pivot point P) greater than a distance from pivot point P to either the first or the second flat surfaces 131, 132, which causes a toggle action and snap, under cable tension, when moving from a cammed surface 130 engagement with the proximal end 133 to either a first or a second flat surface 131, 132 engagement with the proximal end 133, thereby providing a user with a positive and certain positioning (engagement or disengagement) of the lock slide assembly 18 for each of the lateral and medial hinge assemblies 14, 14*a*.

Accordingly, each cable 78, when positioned in retraction, independently exerts a force greater than that of the corresponding distal biasing spring 85 to assure a force necessary to fully disengage the lock slide 44. The proximal terminal 119, the proximal compression spring 120, the locknut 121, and the distal terminal 122, enable independent adjustment of cable length and cable tensioning, thereby allowing an independent fine-tuning of each of the respective cable release mechanisms 20*a*.

The lever 114, due to the cammed surface 130, linearly translates the cables a distance greater than that necessary to disengage the lock slide 44 from each hinge assembly 14, 14*a*, and does so without over-tensioning the respective cable 78. Over-tensioning is prevented due to an over-travel allowed by a greater deflection of the proximal compression spring 120. The proximal compression spring 120 also serves to tension each cable 78 to hold (bias) one of the first or the second flat surfaces 131, 132 against the proximal end 133 of the upper member 15, thereby providing the user a positive sensory and auditory feedback (snap) upon engagement, and ensuring that the cam-lock feature is fully actuated in either the engaged (locked) or disengaged (unlocked) position.

When the lever 114 is "raked" back (as shown in FIG. 8), the second flat surface 132 (with distance from the pivot point P greater than that of the first flat surface 131) is adapted to hold the cable in a "proximally pulled" position to hold the lock slide 44 in a fully disengaged position relative to the ROM disk 34 and the spring housing 38. The proximal compression spring 120 can be adjusted to avoid an over-tensioning of the cable 78 due to the excess travel. When the lever 114 is "knuckled" forward, relative to the patient, the first flat surface 131 (with distance from the pivot point P less than that of the second flat surface 132) is adapted to enable a more distal positioning of the tensioned cable 78, first decompressing the proximal compression spring 120, then permitting the lock slide 44 to remain in a fully engaged position relative to the ROM disk 34 or the spring housing 38.

Figure 9A:
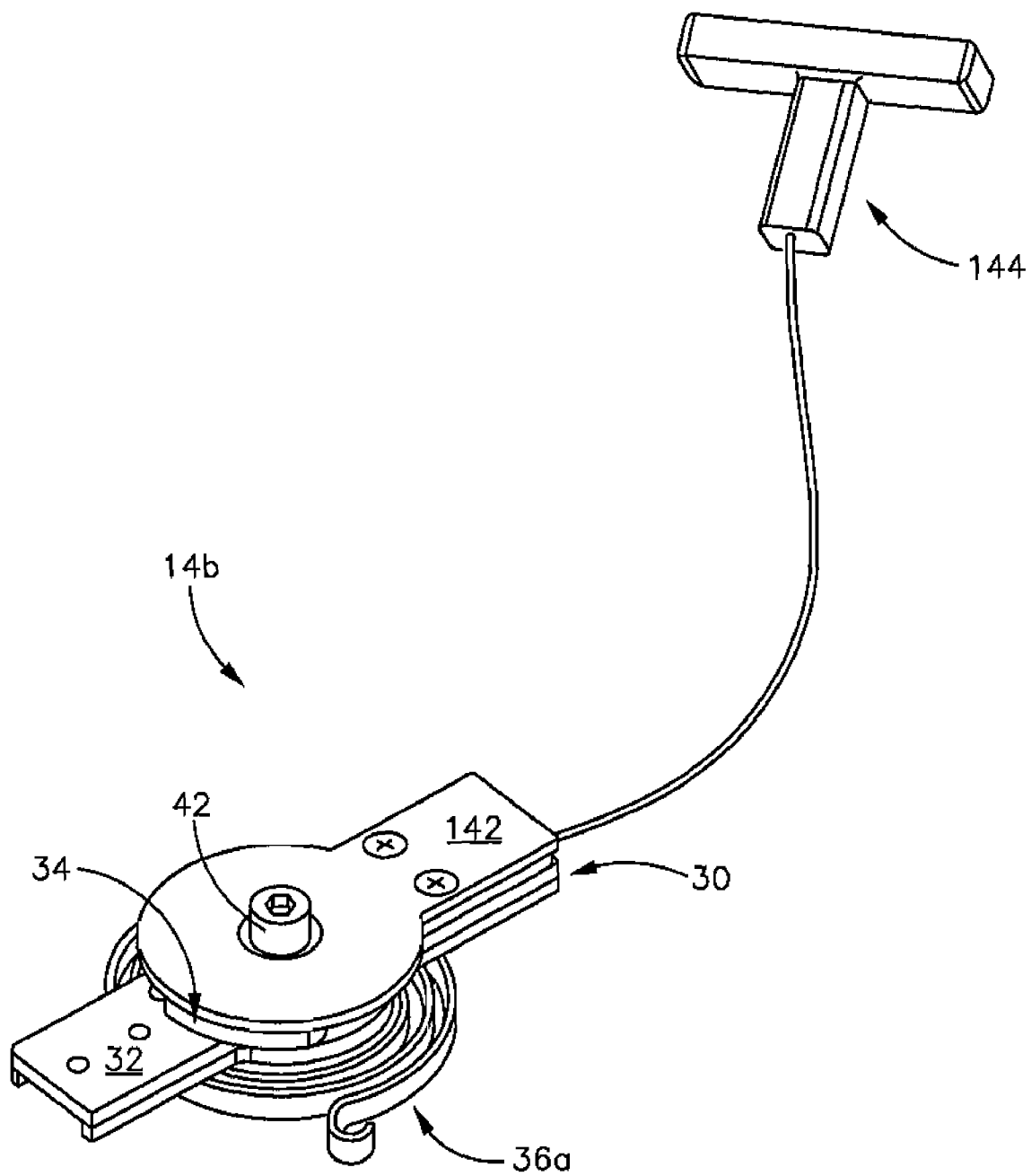
FIG. 9a illustrates an overhead, or front-side, perspective view of a hinge assembly employing a torsion spring in accordance with another embodiment of the present invention.
Figure 9B:
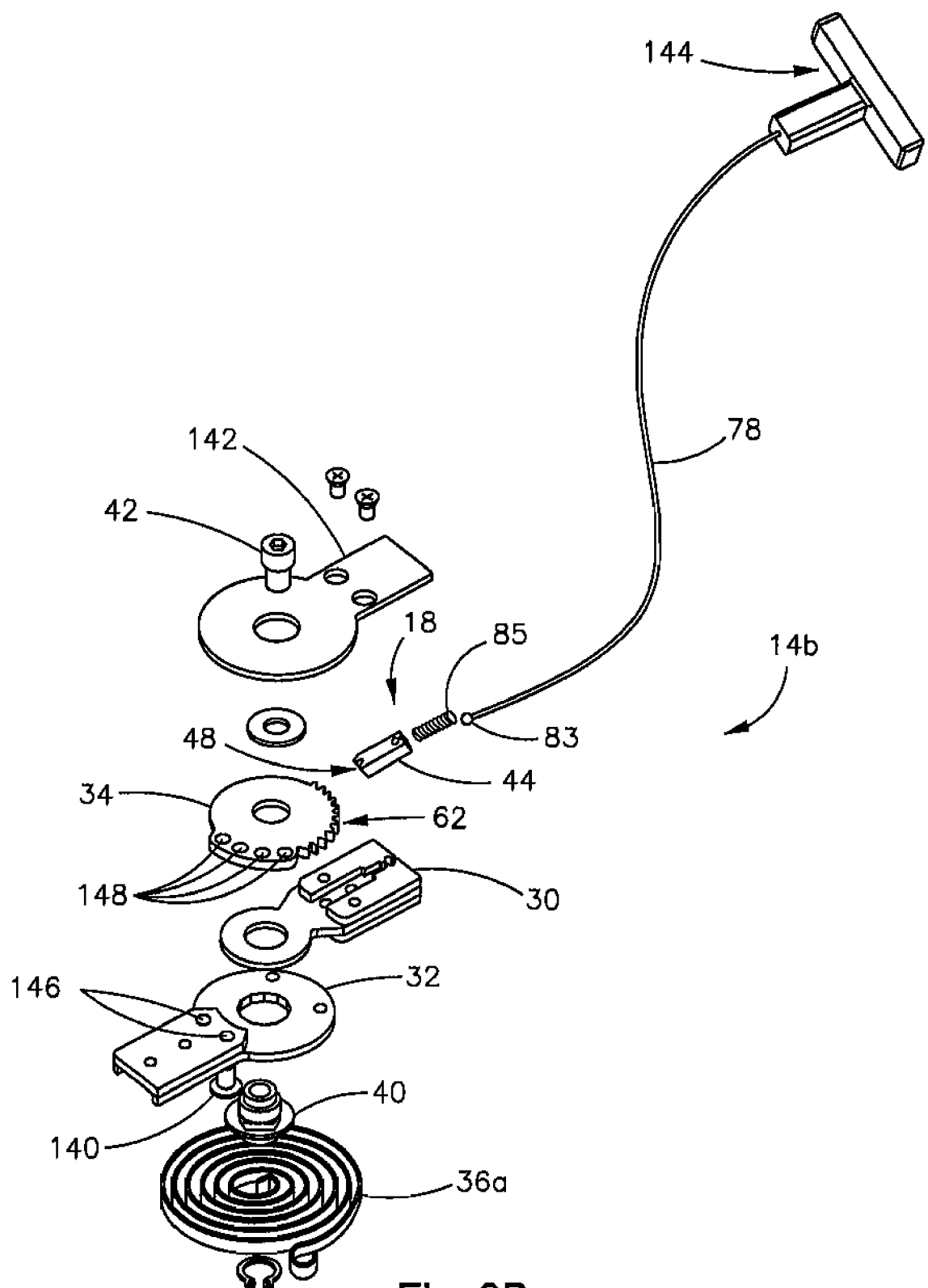

FIGS. 9*a* and 9*b* illustrate a hinge assembly 14*b* embodiment alternative to that shown in FIGS. 3*a*, 3*b*, 7*a*, and 7*b*. This latter hinge assembly 14*b* includes many of the same components and functionality of hinge assemblies 14 and 14*a*, of FIGS. 3*a* and 3*b*, and FIGS. 7*a* and 7*b*, respectively, but does differ in at least a modified ROM disk 34 and a torsional spring 36*a*, described as follows.

Referring to FIG. 9*b*, the hinge assembly 14*b* includes the torsion spring 36*a*, the pivot post 40, a stop pin 140, the distal half joint 32, the proximal half joint 30, the ROM disk 34, a hinge assembly cover 142, the break pin 42, and a handle 144. In this embodiment, the ROM disk 34, when is concentrically aligned with and placed on top of the proximal and distal half joints 30, 32, a top face of the ROM disk 34 lies in a same plane as a top of a raised portion of the proximal half joint 30. The ROM disk 34 is rotatably secured (free to rotate) about a circular portion of the pivot post 40 when the hinge assembly cover 142 is fixedly attached to the raised portion of the proximal half joint 30. The ROM disk includes spur teeth 62 designed to engage slide teeth 48 of the lock slide 44 (as similarly described above for the previous hinge assembly 14, 14a embodiments).

The lock slide 44, the distal biasing spring 85, the cable fitting 83 and the cable 78 (lock slide assembly 18 components) are housed within and cooperate with the proximal half joint 30 as described above for the previous hinge assembly 14, 14a embodiments. In this embodiment, however, a simple handle 144 is used to manipulate the lock slide assembly 18, rather than the cable release mechanisms 20, 20a previously presented.

The stop pin 140 is placed through one of a plurality (two in this embodiment) of stop pin holes 146 in the distal half joint 32, and threaded into one of a plurality (four in this embodiment) of stop pin holes 148 in the ROM disk 34, resulting in the ROM disk 34 and the distal half joint 32 rotating as one about the pivot post 40. Placement of the stop pin 140, as described, provides an adjustable flexion stop (i.e., maximum degree of flexion), preventing a knee (in the case of employment in a knee brace) from buckling past a certain angle. The embodiment of FIGS. 9a and 9b can be adjusted to the following ranges: 0-20°, 0-40°, or 0-60°.

As previously described, the lock slide assembly 18 cooperates with the ROM disk 34 (i.e., biased slide teeth 48 engagement with the spur teeth 62) to provide a one-way, step advance (ratcheting) from predetermined positions of flexion to pre-determined positions of extension (i.e., allowing the hinge assembly 14b to rotate toward full extension (180), but not allowing intermittent rotation toward flexion). If the user desires flexion beyond the pre-set range of motion (e.g., to full flexion for acquiring a sitting position), the slide teeth 48 are disengaged from the spur teeth 62 by pulling the handle 144, which compresses the spring 85 to remove the biasing force of the lock slide 44.

A hex-shaped portion of the pivot post 40 is placed within a 12-sided hole in the distal half joint 32 (an arrangement identical to a 12-point socket and a hex head screw). A bottom of the pivot post 40 is slotted to accept a tang of the torsion spring 36a. Torsion spring 36a tension is augmented by re-indexing (turning) the hex of the pivot post 40 within the dodecagon. A loop, or hook, at an opposite end of the torsion spring 36a communicates with a protruding tab on the proximal half joint 30 or on the upper member 15. Increasing tension increases dampening of shock absorption during heel strike, and further assists a lower limb during the swing phase of gait. This configuration is also suitable for managing joint stiffness and contracture as adjustable tensioning of soft tissues with a torsion spring is very effective.

These and other advantages of the present invention will be apparent to those skilled in the art from the foregoing specification. Accordingly, it is recognized by those skilled in the art that variations or modifications may be made to the above-described embodiments without departing from the broad inventive concepts of the invention. It is therefore understood that this invention is not limited to the particular embodiments described herein, but is intended to include all possible variations and modifications within the scope and spirit of the invention.

What is claimed is:

1. A hinge assembly comprising:
    a first member movably connected to a second member to allow angular displacement of the first member relative to the second member between extension and flexion positions; and
    a spring housing including at least one elastomeric spring, and including at least one mechanism extending into the spring housing and being movable in relation thereto;
    wherein angular displacement of the first member relative to the second member causes a bearing engagement between the at least one mechanism and the at least one elastomeric spring resulting in compression of the at least one elastomeric spring within the spring housing and against the at least one mechanism;
    wherein the compression of the at least one elastomeric spring restrains angular displacement of the first member relative to the second member from an extension to a flexion position, or from a flexion to an extension position; and
    wherein decompression of the at least one elastomeric spring within the spring housing and against the at least one mechanism assists angular displacement of the first member relative to the second member from a flexion to an extension position, or from an extension to a flexion position.

2. The hinge assembly of claim 1, wherein the at least one elastomeric spring is adapted to provide a pre-determined force deflection curve in compression and an independent rate of return hysteresis in decompression.

3. The hinge assembly of claim 1, wherein a time rate of compression of the at least one elastomeric spring in response to a certain force is faster than a subsequent time rate of decompression of the at least one elastomeric spring resulting from the certain force.

4. A hinge assembly for an orthotic, prosthetic, or rehabilitative device, comprising:
    a proximal member movably connected to a distal member to allow angular displacement of the proximal member relative to the distal member between extension and flexion positions; and
    a disk and a lock slide communicating with the proximal and the distal members, the lock slide and the disk adapted for engagement to one another; wherein
    engagement of the lock slide with the disk over a first pre-determined range arrests angular displacement of the proximal member relative to the distal member in a direction toward flexion, and provides one-way, ratcheting step-advance in a direction toward extension; and
    angularly displacing the disk relative to the proximal and the distal members over a second pre-determined range provides free angular displacement of the proximal member relative to the distal member in a direction toward flexion and toward extension, the free angular displacement occurring over the second pre-determined range even if the lock slide is positioned for engagement of the disk.

5. The device of claim 4, wherein the lock slide has one or more slide teeth and the disk has a plurality of disk teeth, the one or more slide teeth each geometrically complementing and being selectably engagable with the disk teeth, the lock slide engaging the disk by an interlocking of the slide teeth with the disk teeth.

6. The device of claim 4, wherein the second pre-determined range is adjustable between approximately 0° to 30° of free angular displacement of the proximal member relative to the distal member in a direction toward flexion and toward extension.

7. The device of claim 6, wherein the second pre-determined range occurs when the proximal member is positioned between approximately 150° to 180° relative to the distal member.

8. The device of claim 4, wherein the hinge assembly further includes a worm gear, and the disk includes a plurality of worm teeth, the worm gear and the worm teeth being engagably positioned so that operation of the worm gear engages and turns the worm teeth to angularly displace the disk relative to the proximal and the distal members to set the first and the second pre-determined ranges.

9. The device of claim 8, wherein the lock slide has one or more slide teeth and the disk further includes a plurality of disk teeth, the lock slide engaging the disk by an interlocking of the slide teeth with the disk teeth, the disk teeth and the worm teeth each lying about a perimeter of the disk in a similar plane.

10. The device of claim 4, wherein the first pre-determined range is adjustable between approximately 90° to 120° of angular displacement of the proximal member relative to the distal member in a direction toward flexion and toward extension.

11. The device of claim 4, wherein the first pre-determined range occurs when the proximal member is positioned between approximately 60° to 180° relative to the distal member.

12. The device of claim 4, further comprising a cable release mechanism including:
- an actuator rotatable about an axis and linearly translatable relative to a bearing surface, the actuator having a projecting cam surface and a first and a second operating surface, the cam surface positioned between the first and the second operating surfaces, the cam surface located a greater distance from the axis than the second operating surface, the second operating surface located a greater distance from the axis than the first operating surface; and
- a cable communicating with the actuator and the lock slide;

wherein:
- positioning the first operating surface against the bearing surface positions the cable to allow the lock slide to engage the disk;
- positioning the second operating surface against the bearing surface linearly translates the actuator, relative to the bearing surface, to linearly retract the cable, relative to the hinge assembly, a distance adequate to disengage the lock slide from the disk; and
- positioning the cam surface against the bearing surface linearly translates the actuator, relative to the bearing surface, to linearly retract the cable, relative to the hinge assembly, a distance greater than that necessary for positioning either the first or the second operating surface against the bearing surface, thereby causing a toggle action and snap, under cable tension, when moving through cam surface engagement with the bearing surface to either of the first or the second operating surface engagement with the bearing surface, to provide a user with positive and certain positioning of the cable release mechanism.

* * * * *